United States Patent
Muramatsu et al.

(10) Patent No.: US 7,223,271 B2
(45) Date of Patent: *May 29, 2007

(54) APPARATUS FOR LIGATING LIVING TISSUES

(75) Inventors: Junichi Muramatsu, Akiruno (JP); Tsukasa Kobayashi, Hachioji (JP); Takayuki Suzuki, Yokohama (JP); Tetsuya Yamamoto, Hidaka (JP)

(73) Assignee: Olympus Corporation, Tokyo (JP)

( * ) Notice: Subject to any disclaimer, the term of this patent is extended or adjusted under 35 U.S.C. 154(b) by 548 days.

This patent is subject to a terminal disclaimer.

(21) Appl. No.: 10/067,607

(22) Filed: May 13, 2002

(65) Prior Publication Data

US 2002/0151916 A1   Oct. 17, 2002

(30) Foreign Application Priority Data

Feb. 5, 2001   (JP) ............................. 2001-028483
Oct. 17, 2001   (JP) ............................. 2001-319657

(51) Int. Cl.
*A61B 17/122* (2006.01)

(52) U.S. Cl. ...................... 606/143; 606/139; 606/157
(58) Field of Classification Search .................... None
See application file for complete search history.

(56) References Cited

U.S. PATENT DOCUMENTS

| 3,958,576 | A | * | 5/1976 | Komiya | 606/142 |
| 4,791,707 | A | | 12/1988 | Tucker | |
| 5,242,456 | A | | 9/1993 | Nash et al. | |
| 5,766,189 | A | * | 6/1998 | Matsuno | 606/158 |
| 6,923,818 | B2 | * | 8/2005 | Muramatsu et al. | 606/142 |
| 7,081,121 | B2 | * | 7/2006 | Muramatsu et al. | 606/142 |
| 2002/0045909 | A1 | * | 4/2002 | Kimura et al. | 606/151 |

FOREIGN PATENT DOCUMENTS

| DE | 197 07 382 A1 | 9/1997 | |
| DE | 100 11 292 A1 | 9/2000 | |
| DE | 102 11 049 A1 | 10/2002 | |
| JP | 60-103946 | 6/1985 | |
| JP | 62-170010 | 10/1987 | |
| JP | 2-6011 | 1/1990 | |
| JP | 09289989 | * 11/1997 | ................. 606/139 |
| JP | 2000-271146 | 10/2000 | |
| WO | WO 99/20183 | 4/1999 | |

* cited by examiner

Primary Examiner—Glenn K. Dawson
(74) Attorney, Agent, or Firm—Scully, Scott, Murphy & Presser, P.C.

(57) ABSTRACT

A ligating apparatus includes an introducing tube which can be inserted in a living body cavity, a manipulating wire inserted in the introducing tube in such a manner that the manipulating wire can freely advance or retreat, a clip which is directly joined to a tip end of the manipulating wire, which has a holding portion formed in a tip end of an arm portion extending from the base end, and which has an extending/opening property, and engaging structure disposed in at least one of the base end of the clip and the tip end of the manipulating wire, wherein at least one of the engaging means is deformed and releases engaging of the clip and the manipulating wire, when the clip engages with the tip end of the introducing tube, and a force for detaching the base end of the clip from the tip end of the manipulating wire is applied.

17 Claims, 16 Drawing Sheets

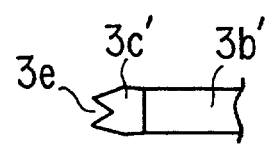
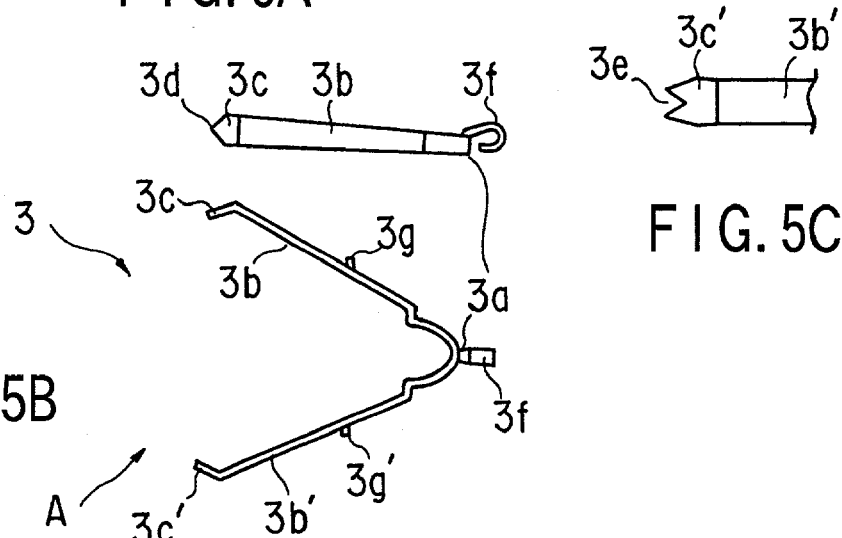
FIG. 5A
FIG. 5C
FIG. 5B
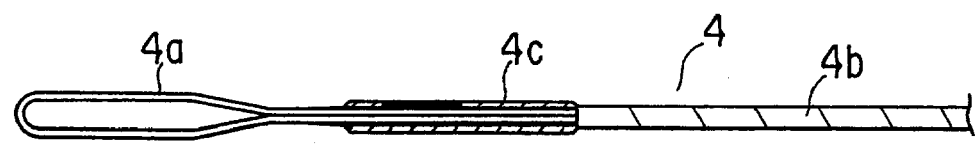
FIG. 6
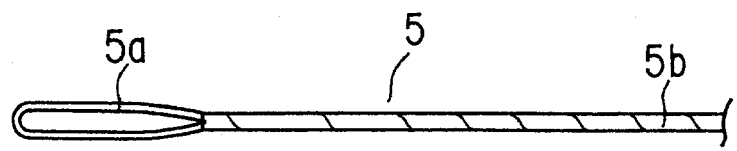
FIG. 7

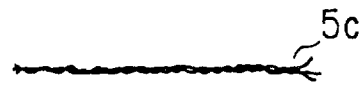
FIG. 8A
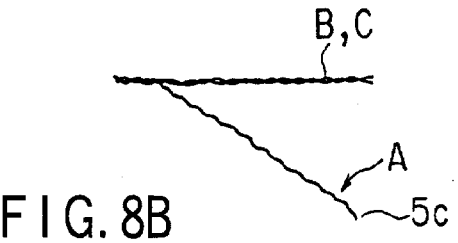
FIG. 8B
FIG. 8C
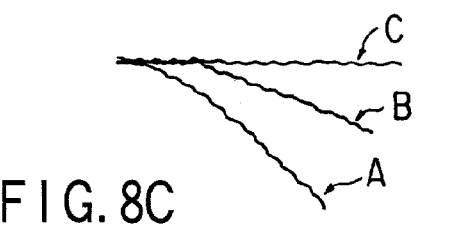
FIG. 8D Enlarged view
FIG. 8E
FIG. 8F Twine wire A back with wires B and C
Twined-back length About 30mm
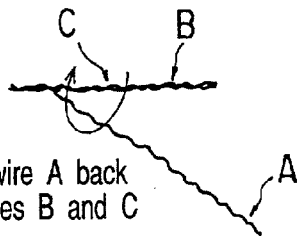
Twine wire A back with wires B and C
FIG. 8G
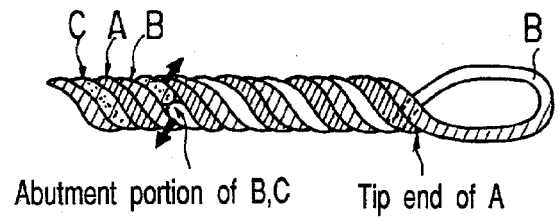
Abutment portion of B,C    Tip end of A
FIG. 8H
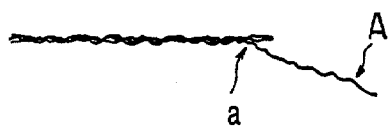
FIG. 8I
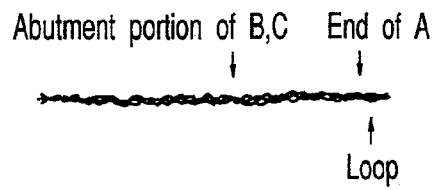
Abutment portion of B,C    End of A
Loop
FIG. 8J FIG. 9A
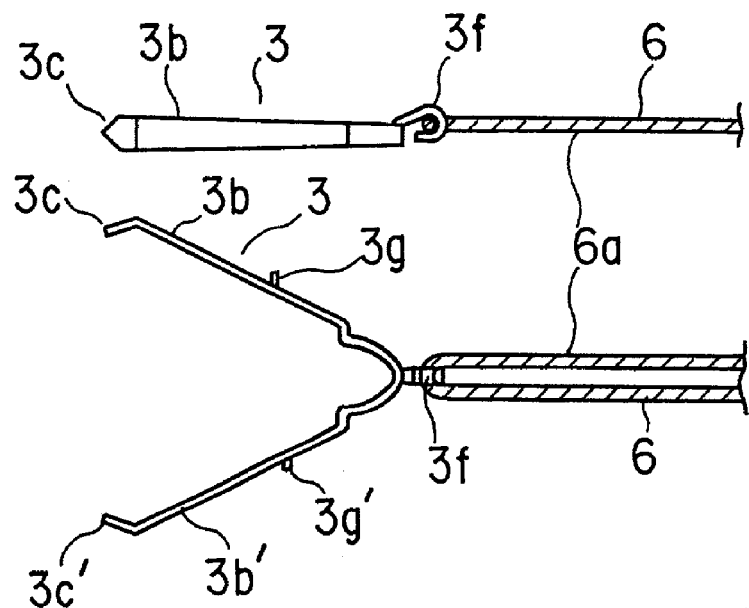
FIG. 9B
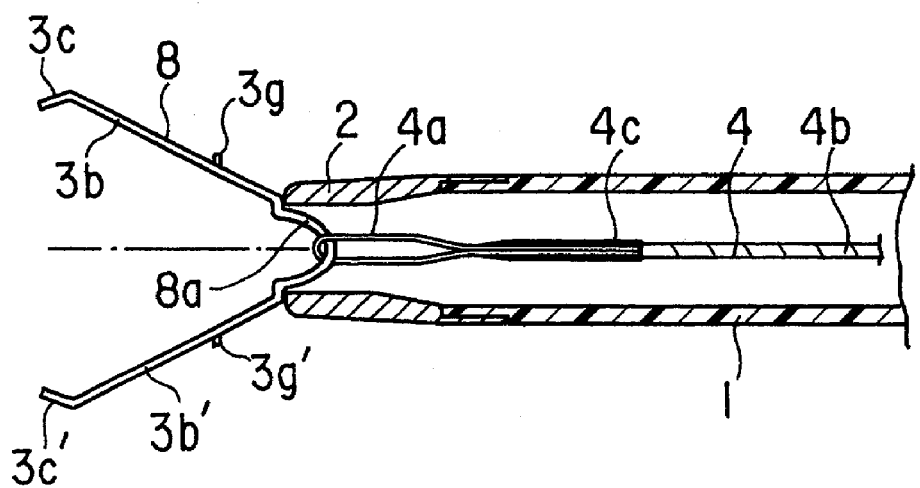
FIG. 10

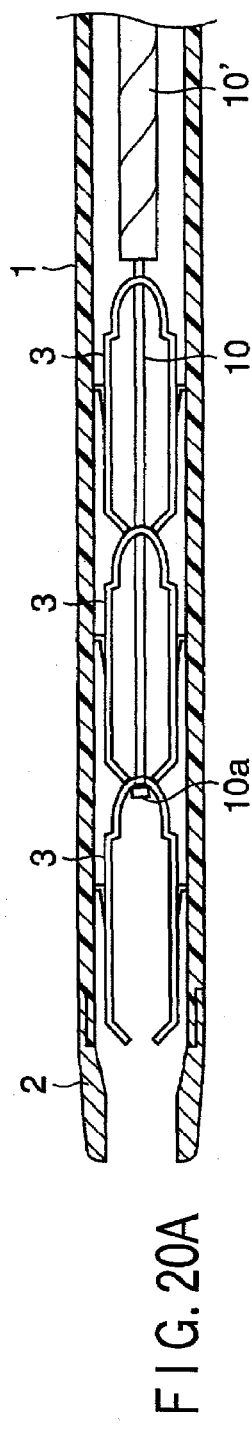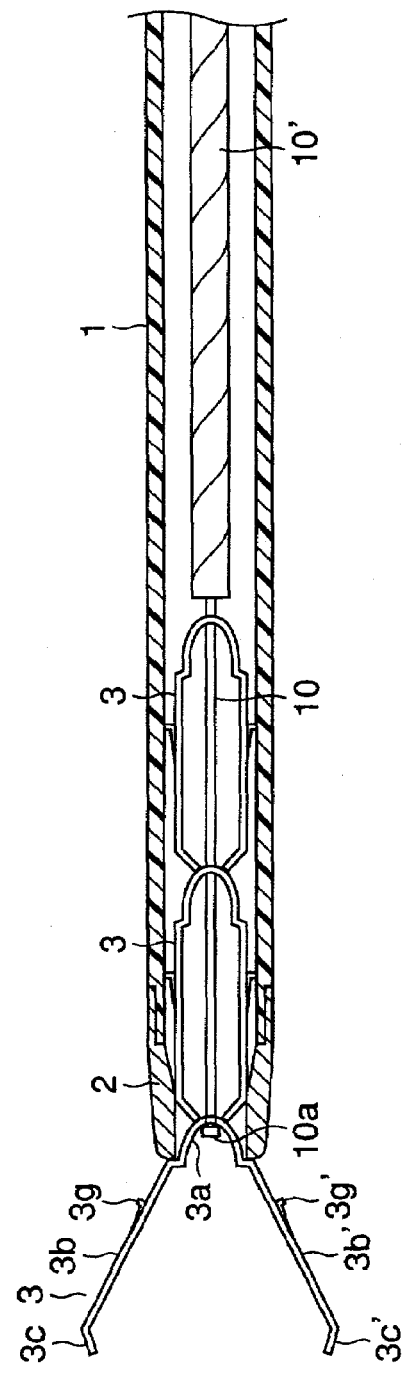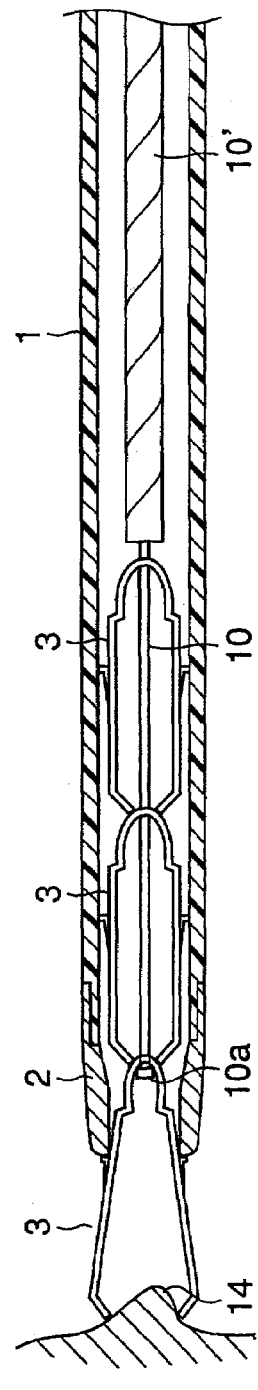
F I G. 20A
F I G. 20B
F I G. 20C

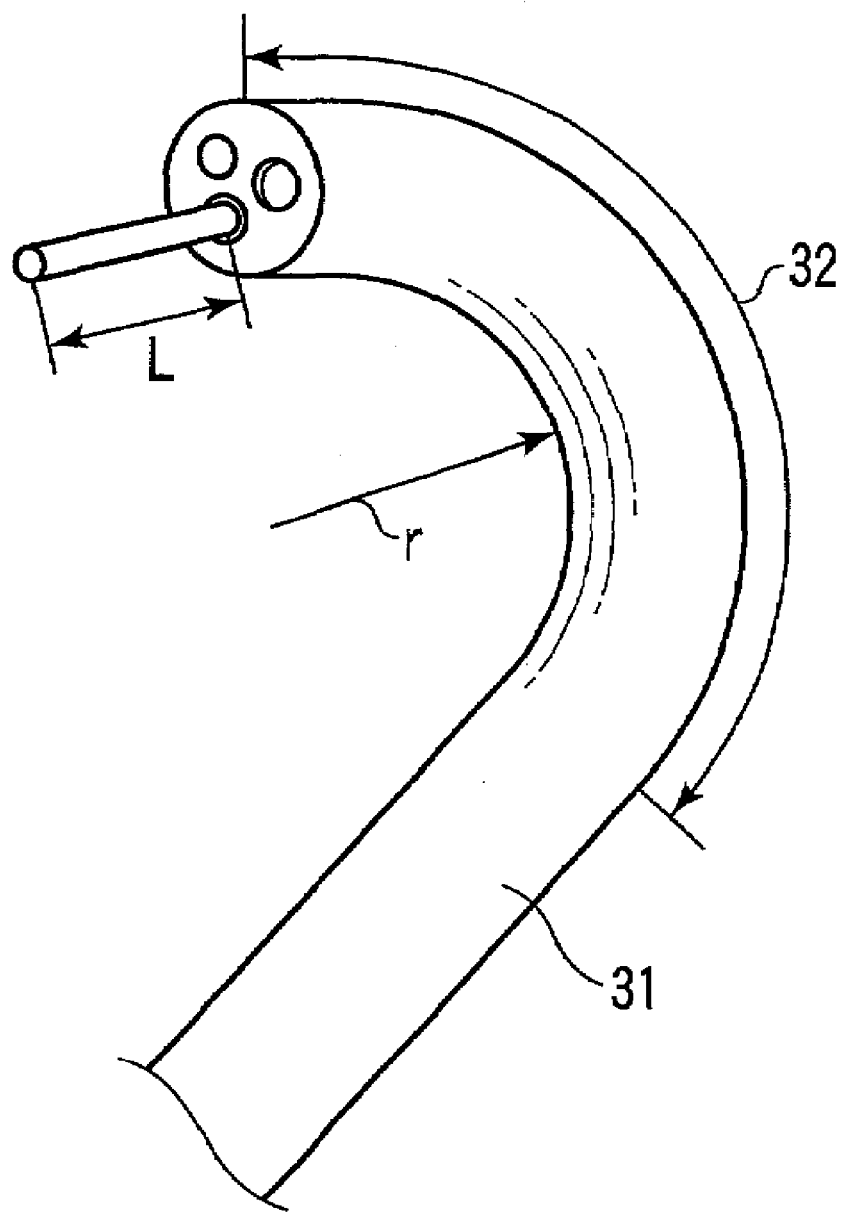
F I G. 20D

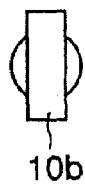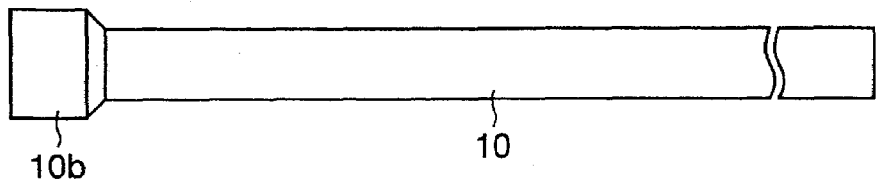
FIG. 24B  FIG. 24A
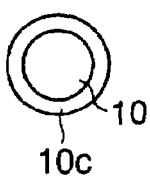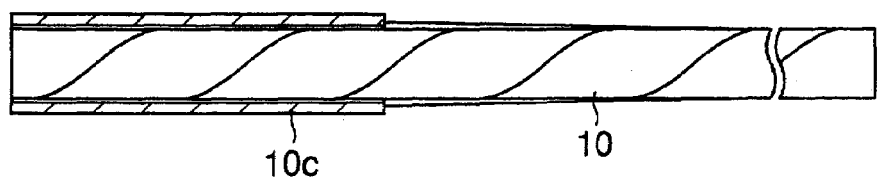
FIG. 25B  FIG. 25A
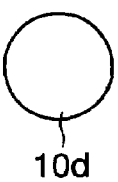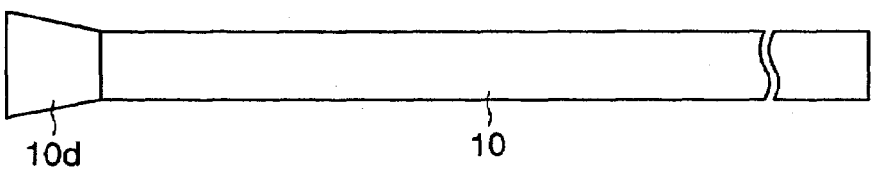
FIG. 26B  FIG. 26A
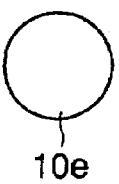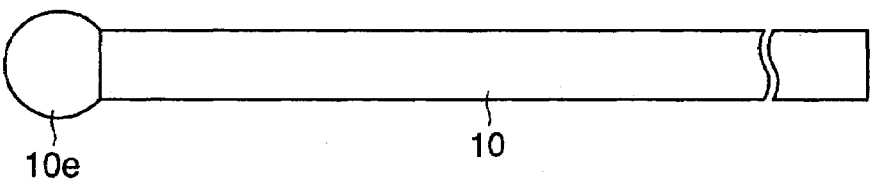
FIG. 27B  FIG. 27A
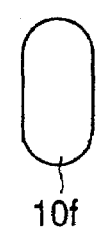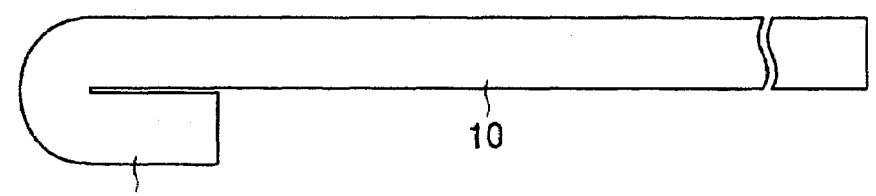
FIG. 28B  FIG. 28A

APPARATUS FOR LIGATING LIVING TISSUES

CROSS-REFERENCE TO RELATED APPLICATIONS

This application is based upon and claims the benefit of priority from the prior Japanese Patent Application(s) No. 2001-28483, filed Feb. 5, 2001 and No. 2001-319657, filed Oct. 17, 2001, the entire contents of which are incorporated herein by reference.

BACKGROUND OF THE INVENTION

1. Field of the Invention

The present invention relates to a ligating apparatus which is endoscopically inserted in a living body cavity and holds living tissues with a clip.

2. Description of the Related Art

Known examples of an apparatus for ligating living tissues are described in Jpn. Pat. Appln. KOKAI Publication No. 60-103946 and Jpn. UM Appln. KOKAI Publication Nos. 62-170010 and 2-6011, and the like.

In Jpn. Pat. Appln. KOKAI Publication No. 60-103946, a clip is attached to a manipulating wire via an eye disposed in a base end of the clip and a hook disposed in a tip end of the manipulating wire. A clip tightening ring is attached to an arm portion of the clip. The base end of the clip tightening ring can be attached to the tip end of a manipulating tube inserted through an introducing tube in such a manner that the tube can freely advance or retreat. During ligating, the clip is projected from the introducing tube, and the manipulating wire is drawn. In this case, when the eye disposed in the base end of the clip is extended, the clip is detached from the manipulating wire, and the clip can be fastened into the living tissues.

In Jpn. UM Appln. KOKAI Publication No. 62-170010, the clip is attached to the manipulating wire via a connection plate which is disposed between the eye disposed in the base end of the clip and the hook disposed in the tip end of the manipulating wire. Similarly as in Jpn. Pat. Appln. KOKAI Publication No. 60-103946, during ligating, the clip is projected from the introducing tube and the manipulating wire is drawn. In this case, when the eye disposed in the base end of the clip is extended, the clip is detached from the manipulating wire, and the clip can be fastened into the living tissues.

In Jpn. UM Appln. KOKAI Publication No. 2-6011, the clip is attached to the manipulating wire via the hook disposed in the tip end of the manipulating wire, and a connection member which is disposed in the tip end of the hook and has the eye. Similarly as Jpn. Pat. Appln. KOKAI Publication No. 60-103946, during ligating, the clip is projected from the introducing tube and the manipulating wire is drawn. In this case, when the eye disposed in the tip end of the connection plate is extended, the clip is detached from the manipulating wire, and the clip can be fastened into the living tissues.

As described above, in the conventional ligating apparatus, engaging components such as the hook and connection member are necessary in an engaging portion of the manipulating wire and clip. Thereby, the number of components increases, and the manufacturing cost increases disadvantageously.

Moreover, to fasten a first clip in the living tissues and continuously fasten a second clip in the living tissues, a clip apparatus is once extracted from an endoscope channel. Moreover, after the clip is attached to the tip end of the manipulating wire, the clip has to be inserted again in the channel of the endoscope. In this case, since the conventional clip apparatus has an engaging component between the clip and the manipulating wire, much time is required in the attachment manipulating of the clip, and the manipulating is very laborious.

BRIEF SUMMARY OF THE INVENTION

The present invention has been developed in consideration of the above-described circumstances, and an object thereof is to provide a ligating apparatus in which a clip is directly attached to a manipulating wire, the number of components is thereby decreased in an engaging portion of the clip and manipulating wire, the manufacturing cost is reduced, and an attachment manipulating of the clip is facilitated during manufacturing.

Another object of the present invention is to provide a ligating apparatus in which a first clip is fastened in living tissues, and a second and subsequent clips can be fastened without extracting a clip apparatus from an endoscope channel.

According to one aspect of the present invention, there is provided a ligating apparatus comprising an introducing tube which can be inserted in a living body cavity; a manipulating wire inserted through the introducing tube in such a manner that the manipulating wire can freely advance or retreat; and a clip which has a base end and a holding portion formed in a tip end of an arm portion extending from the base end and has an opening/extending property, and whose base end is directly attached to the tip end of the manipulating wire. When the clip is attached to the tip end of the introducing tube, and a force is applied in a direction to detach the base end of the clip from the tip end of the manipulating wire, at least one engaging means disposed in at least one of the base end of the clip and the tip end of the manipulating wire is deformed, and engaging of the clip and the manipulating wire is released.

According to another aspect of the present invention, there is provided a ligating apparatus comprising an introducing tube which can be inserted in a living body cavity; a manipulating wire inserted through the introducing tube in such a manner that the manipulating wire can freely advance or retreat; and at least two clips each of which has a base end and a holding portion formed in a tip end of an arm portion extending from the base end. The two or more clips are arranged in series, a hole through which the manipulating wire can be inserted is formed in the base end of each clip, and a bulged portion larger than the hole is disposed in the tip end of the manipulating wire inserted through the hole in the base end of the Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 5A is a plan view showing the clip in the first embodiment.

FIG. 5B is a side view showing the clip in the first embodiment.

FIG. 5C is a view seen from an arrow A direction of FIG. 5B.

FIG. 6 is a side view of a manipulating wire according to the first embodiment.

FIG. 7 is a side view of the manipulating wire according to a second embodiment of the present invention.

FIGS. 8A to 8J are explanatory views of a manufacturing method of the manipulating wire according to the second embodiment.

FIG. 9A is a plan view of the clip and manipulating wire according to a third embodiment of the present invention.

FIG. 9B is a side view of the clip and manipulating wire according to the third embodiment.

FIG. 10 is a longitudinal side view of the tip end in the ligating apparatus according to a fourth embodiment of the present invention.

FIGS. 20A to 20D are longitudinal side views showing the action of the clip apparatus according to an eleventh embodiment of the present invention, and FIG. 20D is a perspective view of the tip end of an endoscope.

FIG. 24A is a side view showing a bulged portion of a fifteenth embodiment of the present invention.

FIG. 24B is a front view of the bulged portion.

FIG. 25A is a side view showing a different example of the bulged portion.

FIG. 25B is a front view of the bulged portion.

FIG. 26A is a side view showing another example of the bulged portion.

FIG. 26B is a front view of the bulged portion.

FIG. 27A is a side view showing another example of the bulged portion.

FIG. 27B is a front view of the bulged portion.

FIG. 28A is a side view showing another example of the bulged portion.

FIG. 28B is a front view of the bulged portion.

DETAILED DESCRIPTION OF THE INVENTION

Respective embodiments of the present invention will be described hereinafter with reference to the drawings.

Figure 1:
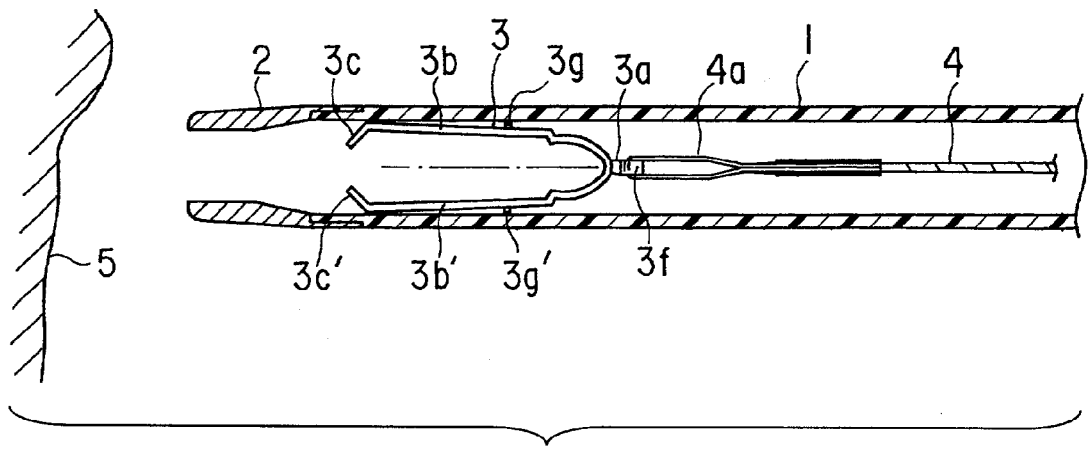
FIG. 1 is a longitudinal side view of a tip end in a ligating apparatus according to a first embodiment of the present invention.
Figure 2:
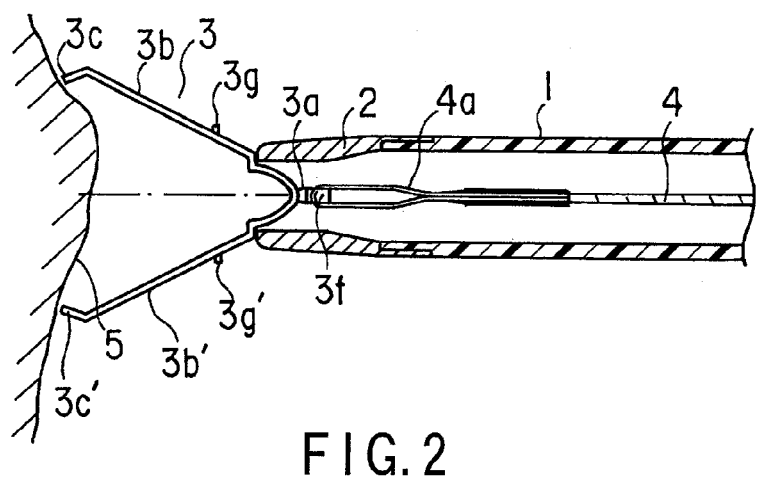
FIG. 2 is a longitudinal side view of a projecting state of a clip in the first embodiment.
Figure 3:
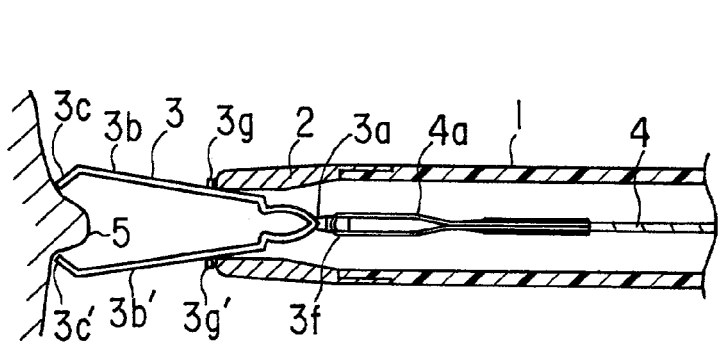
FIG. 3 is a longitudinal side view showing that a living tissue is held with a clip in the first embodiment.

FIGS. 1 to 6 show a first embodiment, and FIGS. 1 to 3 are longitudinal side views of a tip end in a ligating apparatus. An introducing tube 1 has flexibility such that the tube can be inserted in a channel of an endoscope, and a tip-end chip 2 is disposed in the tip end of the introducing tube 1. The tip-end chip 2 is welded, bonded, or pressed, and fixed to the tip end of the introducing tube 1. A manipulating wire 4 is inserted in the introducing tube 1 in such a manner that the wire can freely advance or retreat, and a clip 3 is disconnectably connected to the tip end of the manipulating wire 4 so that the clip can freely project or retract with respect to the tip end of the introducing tube 1.

The introducing tube 1 is a coil sheath whose inner and outer surfaces with a metal wire (such as stainless steel) having a circular section closely wound therearound have concaves/convexes. Through such a structure, even when a force for compressing the sheath is applied to the tip end and base end of the sheath, the sheath does not buckle.

Moreover, the introducing tube 1 may be a coil sheath which is constituted, for example, by crushing a metal wire (such as stainless steel) having a circular section, setting the wire section to be rectangular, and closely winding the wire around the smooth inner and outer surfaces. In this case, since the inner surface is smooth, the clip 3 can easily be projected and the manipulating wire 4 can easily be inserted. Moreover, as compared with the round coil sheath, even when the same diameter of a material wire is used, a coil sheath having a large inner diameter can be realized. Therefore, the projecting of the clip 3 and the inserting of the manipulating wire 4 are further facilitated.

Furthermore, examples of the introducing tube 1 may include a tube sheath of a polymer resin (synthesized polymer polyamide, high/low density polyethylene, polyester, polytetrafluoroethylene, tetrafluoroethylene-perfluoroalkylivinylether copolymer, tetrafluoroethylene-hexafluoropropylene copolymer, and the like). In this case, since the inner and outer surfaces of the sheath have smoothness, inserting of the sheath into an endoscope channel, projecting of the clip 3, and inserting of the manipulating wire 4 are facilitated.

Additionally, the introducing tube 1 may be a tube sheath formed by disposing and embedding a reinforcing member in a double tube whose wall has inner and outer layers. In this case, the inner and outer layers are formed of the polymer resin. The reinforcing member is made of a cylindrical blade formed, for example, by knitting a fine metal wire in a lattice form. Therefore, as compared with the tube sheath in which the reinforcing member is not embedded, even when the force for compressing the sheath is applied to the tip end and base end of the sheath, the sheath is superior in resistance to compression and does not buckle.

The introducing tube 1 has an outer diameter of such a dimension that the tube can be inserted through the endoscope channel. The thickness of the sheath is determined by rigidity of the material. The metal sheath has a thickness of about 0.2 to 0.7 mm, and the polymer resin tube has a thickness of about 0.3 to 0.8 mm. However, when the reinforcing member is embedded, the thickness can be reduced, and the sheath inner diameter can advantageously be increased.

The tip-end chip 2 is a short tube of a metal (such as stainless steel), and has an outer peripheral surface tapered toward the tip end. This facilitates the inserting of the introducing tube 1 in the endoscope channel. Moreover, the chip also has a tapered inner peripheral surface, and the clip 3 easily projects from the tip-end chip 2. Moreover, the inner diameter of the tip end of the tip-end chip 2 is set to such a dimension that a protrusion disposed in the arm portion of the clip 3 fits in the tip end as described later and the arm portion of the clip 3 can be opened. The tip end of the tip-end chip 2 has an outer diameter of 1.5 to 3.3 mm, and an inner diameter of about 1.0 to 2.2 mm.

For the clip 3, as shown in FIG. 5, a middle portion of a metal thin strip is bent, a bent portion is formed as a base end 3a, and opposite arm portions 3b, 3b' extending from the base end 3a are bent in an extending/opening direction. Moreover, tip-end edges of the arm portions 3b, 3b' are bent and disposed opposite to each other, and formed as holding portions 3c, 3c'. The tip end of one of the holding portions 3c, 3c' is formed in a convex shape 3d, and the other tip end is formed in a concave shape 3e, so that a living tissue 5 (see FIG. 3) can easily be held. Moreover, an opening/extending property is imparted to the arm portions 3b, 3b' so as to open the holding portion 3c. A hook 3f projecting backwards is attached to the base end 3a. The hook 3f is formed by bending the stainless steel strip extending from the base end 3a substantially in a J shape.

Additionally, the respective arm portions 3b, 3b' have projections 3g, 3g' which can be joined to the tip-end chip 2 during ligating with the clip 3 (when the clip base end is pulled into the tip-end chip).

For example, when the thin strip material of the clip 3 is stainless steel having a spring property, the clip has a rigidity and can securely hold the living tissue.

For example, when a super-elastic alloy such as a nickel-titanium alloy is used as the material and the extending/opening property is imparted to the arm portions 3b, 3b', the arm portions 3b, 3b' projecting from the sheath are securely opened.

When a tensile force amount of about 1 to 5 kg is applied to the hook 3f disposed in the base end of the clip 3, the hook 3f cannot maintain the J shape, becomes deformed, and extends substantially in an I shape.

Moreover, the strip of the clip 3 has a thickness of 0.15 to 0.3 mm, and the holding portions 3c, 3c' have a strip width of 0.5 to 1.2 mm. The arm portions 3b, 3b' have a strip width of 0.5 to 1.5 mm. The projections 3g, 3g' have a size of 0.2 to 0.5 mm. The base end 3a has a strip width of 0.3 to 0.5 mm. The hook 3f projects from the base end 3a of the clip 3 by a length of about 1 to 3 mm.

As shown in FIG. 6, the manipulating wire 4 is constituted of a loop wire 4a, and a base end wire 4b. The closed loop wire 4a is molded in the tip end of the base end wire 4b constituted of metal twined wires. The loop wire 4a is formed by one of the twined wires of the base end wire 4b. When a core wire of the twined wires is used in the loop wire 4a, an excellent assembly property is obtained. The core wire may be a twined wire or a single wire. The loop wire 4a is welded or bonded to the base end wire 4b via a metal connection pipe 4c. The loop wire 4a is attached to the hook 3f disposed in the base end 3a of the clip 3, and disposed in the introducing tube 1.

The manipulating wire 4 is, for example, a twined wire of stainless steel. The twined wire has a flexibility comparable with the single wire. Therefore, the flexibility of the introducing tube 1 is not degraded.

A force of 1 to 5 kg is applied to the loop wire 4a during ligating with the clip 3. In this case, the dimension of the loop wire 4a needs to be set such that the wire is not ruptured. The base end wire 4b has an outer diameter of 0.3 to 0.6 mm, and the loop wire 4a has an outer diameter of 0.2 mm or more.

An action of the first embodiment will next be described.

The introducing tube 1 of the clip apparatus is introduced into a body cavity via the channel of the endoscope inserted in the body cavity. As shown in FIG. 1, the tip end of the introducing tube 1 is positioned in the vicinity of the target tissue to be clipped 5 such as a stomach mucous membrane. When the manipulating wire 4 is pushed toward the tip end of the introducing tube 1, the clip 3 is projected from the tip end of the tip-end chip 2. Since the extending/opening property is imparted to the arm portions 3b, 3b' so as to open the holding portions 3c, 3c', the clip 3 is projected from the tip-end chip 2. Moreover, as shown in FIG. 2, the holding portions 3c, 3c' are opened. Furthermore, when the holding portions 3c, 3c' are pressed onto the target tissue 5, and the manipulating wire 4 is drawn, the base end 3a of the clip 3 is pulled into the tip-end chip 2, and the projections 3g, 3g' disposed in the arm portions 3b, 3b' of the clip 3 engage with the tip end of the tip-end chip 2. When the manipulating wire 4 is further drawn, the base end 3a of the clip 3 is plastically deformed. When the holding portions 3c, 3c' are closed, the target tissue 5 can be held as shown in FIG. 3.

Figure 4:
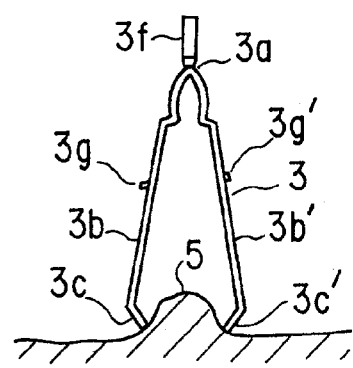
FIG. 4 is a side view showing that the clip is fastened in the living tissue according to the first embodiment.

Here, the manipulating wire 4 is further drawn, and a traction force is applied to the hook 3f attached to the base end 3a of the clip 3. Thereby, the hook 3f bent in the J shape is stretched, the loop wire 4a is detached from the hook 3f, and the manipulating wire 4 is completely detached from the clip 3. Thereby, as shown in FIG. 4, the clip 3 is completely fastened into the target tissue 5.

Moreover, when the holding portions 3c, 3c' of the clip 3 hold the tissue, the target tissue 5 cannot securely be grasped in some case. Alternatively, a tissue different from the targeted tissue is grasped by the clip 3 in other case. In this case, the clip 3 having the holding portions 3c, 3c' once closed is again extended/opened, the tissue is again targeted, and the clip 3 is again closed.

The manipulating wire 4 is slightly drawn from the state shown in FIG. 2. While the tissue is held between the holding portions 3c, 3c' of the clip 3, and the clip 3 needs to be extended/opened again, the opening of the clip is realized by the following action. That is, the manipulating wire 4 is pushed forwards, or pulled toward the base end of the introducing tube 1, so that the arm portions 3b, 3b' of the clip 3 are extended/opened. In this case, the base end 3a of the clip 3 is not plastically deformed yet. Therefore, the arm portions 3b, 3b' of the clip 3 can be extended/opened by an elastic force given beforehand. In this case, the target tissue 5 can be targeted and grasped by the clip 3 again.

According to the first embodiment, when the clip is directly joined to the manipulating wire, the number of components decreases in an engaging portion of the clip and manipulating wire. This can reduce a manufacturing cost. Moreover, the attachment manipulating of the clip during manufacturing is facilitated. Furthermore, after a first clip is fastened in the living tissue, the clip apparatus is extracted from the endoscope channel. When a second clip is attached again, the loop wire is simply attached to the hook of the clip. The clip attachment manipulating is therefore facilitated.

FIGS. 7 and 8A to 8J show a second embodiment. FIG. 7 is a side view of the tip end of the manipulating wire, and FIGS. 8A to 8J show a manufacturing method of the manipulating wire.

The wire having the closed loop portion in the tip end as described in the first embodiment is known in Jpn. Pat. Appln. KOKAI Publication No. 2000-271146.

The loop wire forming a closed loop is joined to the tip end of the manipulating wire via a joint pipe. However, in this structure, the joint pipe for joining the manipulating wire to the loop wire is surely required.

On the other hand, it is already known that the core wire of the twined manipulating wire is used as the loop wire and the closed loop is formed. However, the joint pipe is required for joining the loop wire to the manipulating wire.

Thereby, the number of components increases, and accordingly the number of assembly steps by the joining manipulating such as welding, bonding, and caulking also increases. Moreover, there is a problem that the manufacturing cost increases.

On the other hand, when the joint pipe is disposed, a hard portion is disadvantageously formed in the joint portion of the loop wire and manipulating wire. Since the hard portion is formed, flexibility is lost, and the insertion property of the endoscope into a forceps channel is degraded. Moreover, when the endoscope is angled, the hard portion cannot be inserted through the angled portion of the endoscope, and the clip cannot project from the tip end of the forceps channel as another problem.

Furthermore, since the joint pipe is disposed, the outer diameter of the joint portion of the loop wire and manipulating wire increases. When the outer diameter increases, the clearance from the inner surface of the introducing tube (insertion portion) constituting a treatment tool for the endoscope decreases, and contact resistance also increases. Originally, the inner diameter of the introducing tube as the treatment tool for the endoscope is of the order of 1 to 2.5 mm and very small. There is a problem that even a slight increase in the outer diameter remarkably degrades the insertion property.

To solve the problem, as shown in FIG. 7, a manipulating wire 5 is constituted of a loop wire 5a and base end wire 5b. The base end wire 5b is constituted of a twined wire of a metal, and constituted, for example, by twining three material wires.

Now, a method for manufacturing the manipulating wire 7 (for example, manufacturing method using 1×3 twisted wires) will be described with reference to FIG. 8A to FIG. 8J. The outer diameter of the wire is about 0.3 mm to 0.6 mm in diameter.

1. A wire end portion 8c is loosened as shown in FIG. 8A.
2. One of the three wires, i.e., wire A is loosened while it is turned, as shown in FIG. 8B. At this time, a length of about 60 mm is loosened from the wire end portion 7c similarly.
3. Second wire B or C is loosened similarly as shown in FIG. 8C. At this time, a length of about 60 mm is loosened from the wire end portion 7c similarly.
4. Second wire B or C is folded as shown in FIG. 8D. At this time, a folded end X and a loosened end Y must be spaced sufficiently from each other. In addition, it is more easier to fold the wire at a top portion when it is rounded, as shown in enlarged view.
5. The folded wire B is turned and twisted in the loosing direction, as shown in FIG. 8E (in the case of Z twisting). At this time, a deformed end portion is cut in advance before twisted. As shown in FIG. 8F, the twist-back length is about 30 mm.
6. As shown in FIG. 8F, wire C is twisted back to wire B, and the wire is cut at a location of the folded end of wire B. At this time, wires C and B are provided so as not to be spaced and superimposed. (This is because wire A easily slips when it is returned).
7. As shown in FIG. 8G, wire A is twisted back to wires B and C. At this time, it is desirable that an abutment portion between wire C and wire B be observed under a substance microscope. In addition, care must be taken so that wire C and wire B do not move when a portion forward or backward of the abutment portion is twisted.

Further, as shown in FIG. 8H, when wire A is loaded, care must be taken so as not to flip wires B and C in a direction indicated by the filled arrow. Wire A is easily loaded by placing the wire at a distal end side (loop side) relevant to the abutment portion of wires B and C.

8. As shown in FIG. 8I, wire A is cut at the extremity of the loop (portion "a").
9. As shown in FIG. 8J, cutting is completed. The loop is defined as about 5 mm in length. In addition, the abutment portion of wires B and C and the end portion of wire A may be prevented from looseness of twist by means of welding, adhesive, or any other method.

Working of a second embodiment is identical to that of the first embodiment. A duplicate description is omitted here.

Since the action of the second embodiment is the same as that of the first embodiment, the description thereof is omitted.

According to the second embodiment, as compared with the manipulating wire 4 of the first embodiment, since the connection pipe 4c is not disposed, the number of components decreases, accordingly the number of assembly steps by the joining manipulating such as welding, bonding, and caulking can also be decreased, and therefore, the manufacturing cost can be reduced. Moreover, since the outer diameter is not enlarged even in the joint portion of the base end wire 5 and loop wire 5a, friction resistance with the inner surface of the introducing tube 1 does not increase, and the insertion property of the manipulating wire 5 is kept. Thereby, the clip 3 can easily be projected from the introducing tube 1. Moreover, since the hard portion is not formed in the joint portion of the loop wire and manipulating wire, the flexibility can be maintained, and the insertion property of the endoscope into the forceps channel can be held.

FIGS. 9A, 9B show a third embodiment, the same constituting portions as those of the first embodiment are denoted with the same reference numerals, and the description thereof is omitted. FIG. 9A is a plan view of the clip and manipulating wire, and FIG. 9B is a side view. A manipulating wire 6 is formed by bending the tip end of the wire in a flat loop shape and joining the tip end to the hook 3f of the clip 3, and two manipulating wires 6 are inserted into the base end of the introducing tube 1.

The manipulating wire 6 may be coated with a polymer resin 6a having excellent slippage, such as high/low density polyethylene, and polytetrafluoroethylene. The thickness of the coating is optimum in a range of about 0.05 mm to 0.1 mm. Furthermore, to enhance the slippage of the manipulating wire 6, the wire surface is subjected to embossment of 0.01 mm to 0.45 mm, or may effectively be coated with a silicone oil. The manipulating wire 6 is a twined or single wire of a metal such as stainless steel, and has an outer diameter of about 0.2 to 0.5 mm.

The action of the third embodiment includes: drawing two manipulating wires 6 altogether. Other actions are the same as those of the first embodiment, and the description thereof is omitted.

According to the third embodiment, as compared with the first and second embodiments, the clip can be joined to the manipulating wire with a simpler constitution. Since the wire is coated with the polymer resin 6a, the slippage of the manipulating wire is enhanced, the friction resistance with the inner surface of the introducing tube decreases, and the traction force amount can be transmitted to the tip end of the introducing tube without any loss, so that the ligating manipulation can be performed with a smaller force.

FIG. 10 shows a fourth embodiment, the same constituting portions as those of the first embodiment are denoted with the same reference numerals, and the description thereof is omitted.

A clip 8 of the fourth embodiment is constituted by omitting the hook 3f of the clip 3 of the first embodiment, bending the clip substantially in a U shape, and joining the loop wire 4a directly to a base end 8a of the clip 8. Moreover, the diameter of the loop wire 4a is set to about 0.1 to 0.2 mm.

The action of the fourth embodiment will next be described.

When the holding portions 3c, 3c' are brought close to the target tissue 5, the manipulating wire 4 is drawn. The arm portions 3b, 3b' of the clip 8 bent in the extending/opening direction engage with the tip end of the tip-end chip 2. Here, when the holding portions 3c, 3c' are pressed onto the target tissue 5 and the manipulating wire 4 is further drawn, the arm portions 3b, 3b' of the clip 8 are pulled in the tip-end chip 2, the holding portions 3c, 3c' are closed, and the target tissue 5 can be held. Furthermore, when the manipulating wire 4 is drawn, the loop wire 4a is ruptured. A force of 1 to 5 kg is applied to the loop wire 4a during ligating with the clip 8. The dimension is set such that the loop wire 4a is ruptured with the application of the force.

When the loop wire 4a is ruptured, the clip 8 is disengaged from the manipulating wire 4, and the clip 3 can be fastened in the living tissue.

Additionally, in the fourth embodiment, wince the loop wire 4a is ruptured, the clip 8 is disengaged from the manipulating wire 4. As a modification example, in the loop wire shown in FIG. 8F, the twined-back length of the wire B is set to be short, and the loop is untwined during ligating, so that the clip 8 may be disengaged from the manipulating wire 4. An appropriate twined-back length is in a range of about 5 to 10 mm.

According to the fourth embodiment, as compared with the first embodiment, since the hook 3f of the base end 8a of the clip 8 is not disposed, the clip can be molded more inexpensively.

Figure 11A:
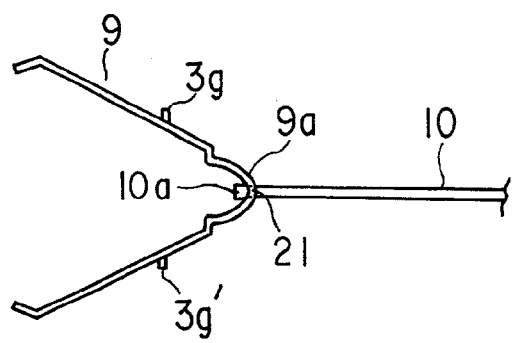
FIG. 11A is a side view of the clip according to a fifth embodiment of the present invention.
Figure 11B:
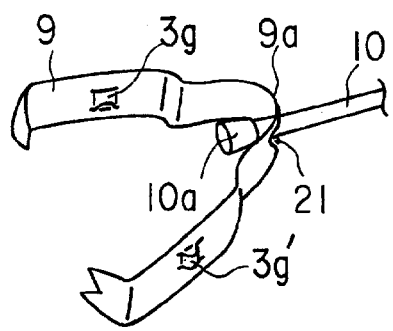
FIG. 11B is a perspective view of the clip according to the fifth embodiment.
Figure 12A:
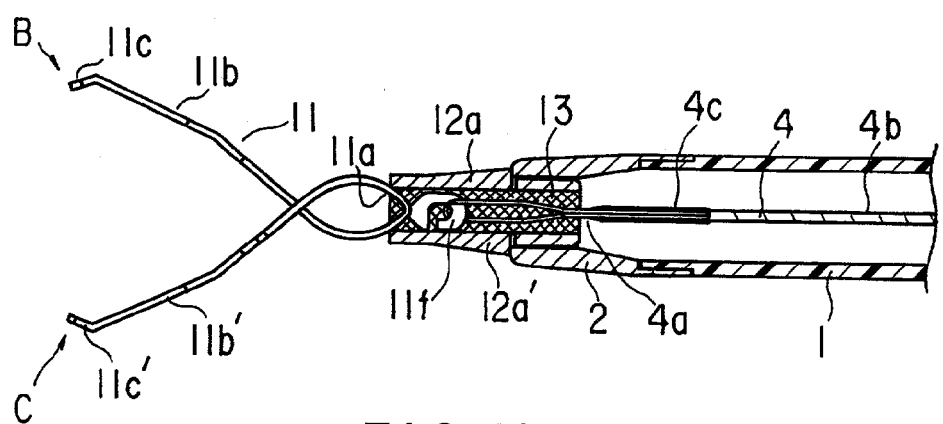
FIG. 12A is a longitudinal side view of a clip apparatus according to a sixth embodiment of the present invention.
Figure 12B:
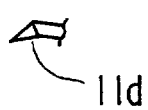
FIG. 12B is a view seen from an arrow B direction of FIG. 12A.
Figure 12C:
FIG. 12C is a view seen from an arrow C direction of FIG. 12A.

FIGS. 11A, 11B show a fifth embodiment, the same constituting portions as those of the first embodiment are denoted with the same reference numerals, and the description thereof is omitted.

A clip 9 is constituted by omitting the hook 3f of the clip 3 of the first embodiment, bending the clip substantially in the U shape, and forming a hole 21 for passing a manipulating wire 10 in a base end 9a of the clip 9.

The manipulating wire 10 is a metal single wire, and has a diameter of about 0.2 to 0.7 mm. The manipulating wire 10 is inserted through the hole 21, and a flat bulged portion 10a as a stopper is disposed in the tip end of the manipulating wire 10. Examples of a method for molding the flat bulged portion 10a include caulking, laser, and plasma welding. An appropriate diameter of the hole 21 is in a range of about 0.2 to 0.7 mm. The manipulating wire 10 which can be inserted through the hole 21 is used. The maximum diameter of the flat bulged portion 10a is necessarily larger than the diameter of the hole 21, and is in a range of about 0.25 to 1 mm.

The action of the fifth embodiment will next be described.

When the holding portions 3c, 3c' of the clip 9 are brought close to the target tissue, the manipulating wire 10 is drawn. The arm portions 3b, 3b' of the clip 9 bent in the extending/opening direction engage with the tip end of the tip-end chip 2. Here, when the holding portions 3c, 3c' are pressed onto the target tissue 5 and the manipulating wire 10 is further drawn, the arm portions 3b, 3b' of the clip 9 are pulled in the tip-end chip 2, the holding portions 3c, 3c' are closed, and the target tissue 5 can thereby be held. Furthermore, when the manipulating wire 10 is drawn, the flat bulged portion 10a on the tip end of the manipulating wire 10 is extracted from the hole 21 of the clip base end 3a. Thereby, the diameter of the flat bulged portion 10a is deformed and reduced, or the hole 21 of the base end 3a of the clip 9 is deformed and enlarged, so that the manipulating wire 10 is disengaged from the clip 9. Thereby, the clip 9 can be fastened in the living tissue.

According to the fifth embodiment, the clip is directly joined to the manipulating wire, and the number of components in the engaging portion of the clip and manipulating wire decreases. Thereby, the manufacturing cost is reduced. Moreover, the attachment manipulating of the clip during manufacturing is facilitated.

FIGS. 12A, 12B, 12C to 14 show a sixth embodiment, the same constituting portions as those of the first embodiment are denoted with the same reference numerals, and the description thereof is omitted.

The tip-end chip 2 is welded, bonded, or pressed into the tip end of the introducing tube 1. The tip-end chip 2 is a short tube of a metal (such as stainless steel), and has an outer peripheral surface tapered toward the tip end. Therefore, the inserting of the introducing tube 1 into the endoscope channel can be facilitated.

Moreover, the inner peripheral surface of the tip-end chip 2 is also tapered, and the inner diameter of the tip end is substantially the same in dimension as the outer diameter of a clip tightening ring described later. This suppresses looseness of the clip tightening ring. The outer diameter of the tip edge of the tip-end chip 2 is in a range of 1.5 to 3.3 mm, and the inner diameter of the tip edge of the tip-end chip 2 is in a range of about 1.0 to 2.2 mm.

Furthermore, a clip 11 is formed by bending a thin metal strip at a middle portion, forming the curved portion as a base end 11a, and allowing opposite arm portions 11b, 11b' extending from the base end 11a to intersect each other. Furthermore, the tip edges of the respective arm portions 11b, 11b' are bent so that the tip edges are disposed opposite to each other as holding portions 11c, 11c'. For the tip ends of the holding portions 11c, 11c', one end is formed in a convex shape 11d, and the other end is formed in a concave shape 11e, so that the living tissue is easily grasped. Moreover, the extending/opening property is imparted to the arm portions 11b, 11b' so as to open the holding portions 11c, 11c'. A hook 11f projecting rearwards is attached to the base end 11a. The hook 11f is formed by molding the strip beforehand in a J shape, and bending the strip at the base end 11a.

Examples of the material of the thin strip constituting the clip 11 include stainless steel which has the spring property, and rigidity and which can securely grasp the living tissue. The examples also include a super-elastic alloy such as a nickel-titanium alloy. When the extending/opening property is imparted to the arm portions, the arm portions of the clip projecting from the sheath open more securely.

When a tensile force amount of about 1 to 5 kg is applied to the hook 11f disposed in the base end of the clip 11, the hook 11f cannot maintain the J shape, is deformed, and extends substantially in an I shape.

Moreover, the thickness of the strip of the clip 11 is in a range of 0.15 to 0.3 mm. The holding portion has a strip width of 0.5 to 1.2 mm. The arm portion has a strip width of 0.5 to 1.5 mm. The base end has a strip width of 0.3 to 0.5 mm. The hook projects from the clip base end by a length of about 1 to 3 mm.

A clip tightening ring 12 disposed in the base end of the clip 11 is molded of a resin, metal, or the like which has strength and elasticity. Additionally, a pair of blades 12a, 12a' are disposed in a ring outer peripheral portion such that the blades are elastically deformed and can freely project or retract in a circumferential direction. The number of blades 12a, 12a' is not limited to two, and three or four blades may be used.

When an external force is applied to the circumferential surface of the clip tightening ring 12 in a vertical direction, the blades 12a, 12a' are folded in the inner surface of the tightening ring. Since the blades 12a, 12a' contact the inner surfaces of the introducing tube and tip-end chip 2, inclined surfaces 12b, 12b' are formed on the tip end side. The ring can smoothly be pushed out of the introducing tube 1 and tip-end chip 2 without any resistance.

When the clip tightening ring 12 is attached to the arm portions 11b, 11b' of the clip 11, the arm portions 11b, 11b' of the clip are closed. The ring has a substantially tubular shape. The clip 11 is joined to the manipulating wire 4 by attaching the loop wire 4a to the hook 11f. Additionally, even when the clip 11 is pushed out by the manipulating wire 4, the engaging of the clip 11 and manipulating wire 4 is held, and the clip 11 and clip tightening ring 12 can tentatively be fixed. In this manner, a polymer material such as silicone 13 is fitted in the clip tightening ring 12.

The blades 12a, 12a' of the clip tightening ring 12 may be disposed in the introducing tube 1 in the folded state. However, when the blades 12a, 12a' are disposed in projecting states, the elasticity of the blades 12a, 12a' can be maintained over a long period. Moreover, since the contact resistance between the inner surface of the introducing tube 1 and the blades decreases, the force amount for moving the clip 11 in the introducing tube 1 can also be decreased.

The clip tightening ring 12 is molded by injecting resins having strength and elasticity (polybutylterephthalate, polyamide, polyphenyl amide, liquid crystal polymer, polyether ketone, polyphthal amide). Alternatively, the ring is molded by injecting, cutting, or plasticizing metals having elasticity (super-elastic alloy such as stainless steel, and nickel-titanium alloy).

The tubular portion of the clip tightening ring 12 has an inner diameter of 0.6 to 1.3 mm, and outer diameter of about 1.0 to 2.1 mm. When the blades 12a, 12a' are projected, the diameter of an outermost diametric portion is set to 1 mm or more in consideration with the engaging with the tip-end chip 2.

The action of the sixth embodiment will next be described.

While the body cavity is observed with the endoscope, the tip end of the introducing tube 1 is guided to a target site. The clip 11 and clip tightening ring 12 disposed in the introducing tube 1 are projected from the tip-end chip 2. This is realized by pushing the manipulating wire 4 toward the tip end of the introducing tube 1. The blades 12a, 12a' of the clip tightening ring 12 are folded when passed through the tip-end chip 2. However, the blades 12a, 12a' are passed through the tip-end chip 2, and again projected. Thereby, the clip tightening ring 12 is prevented from entering the tip-end chip 2 again.

When the holding portions 11c, 11c' of the clip 11 are brought close to the target tissue, and the manipulating wire 4 is drawn, the blades 12a, 12a' of the clip tightening ring 12 engage with the end surface of the tip-end chip 2. When the manipulating wire 4 is further drawn, an elliptic portion of the base end 11a of the clip 11 is pulled into the clip tightening ring 12. Here, since the dimension of the elliptic portion is larger than the inner diameter of the clip tightening ring 12, the elliptic portion is ruptured by the clip tightening ring 12. Then, the arm portions 11b, 11b' are largely extended/opened outwards.

Figure 13:
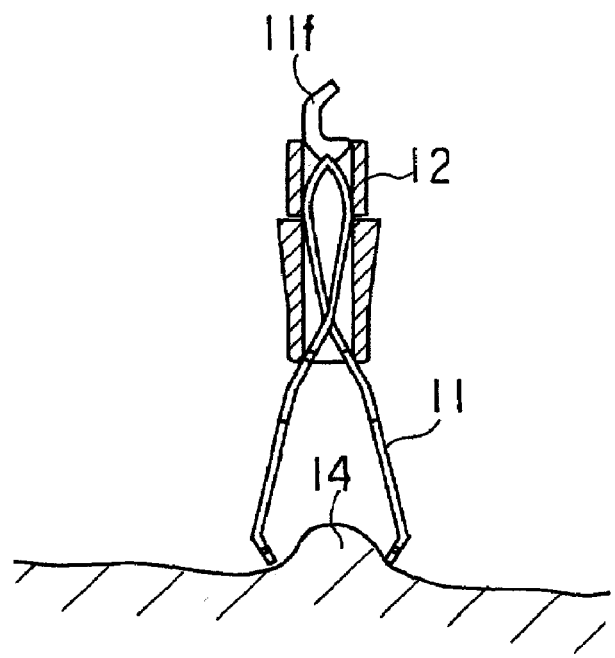
FIG. 13 is a longitudinal side view showing that the clip of the sixth embodiment is fastened in the living tissue.

In this state, as shown in FIG. 13, the clip 11 is guided to hold a target living tissue 14. When the manipulating wire 4 is further drawn, the arm portions 11b, 11b' of the clip 11 are pulled into the clip tightening ring 12, and the holding portions 11c, 11c' of the clip 11 are closed. While the living tissue 14 is securely held by the arm portions 11b, 11b' of the clip, the manipulating wire 4 is further drawn, and the hook 11f is stretched, the engaging of the clip 11 and manipulating wire 4 is released. Thereby, the clip 11 which holds the living tissue 14 can be fastened in the body cavity.

According to the sixth embodiment, in addition to the effect of the first embodiment, the following effect is produced. Since the clip tightening ring confines the arm portions of the clip, the living tissue can be ligated with a stronger force.

Figure 15:
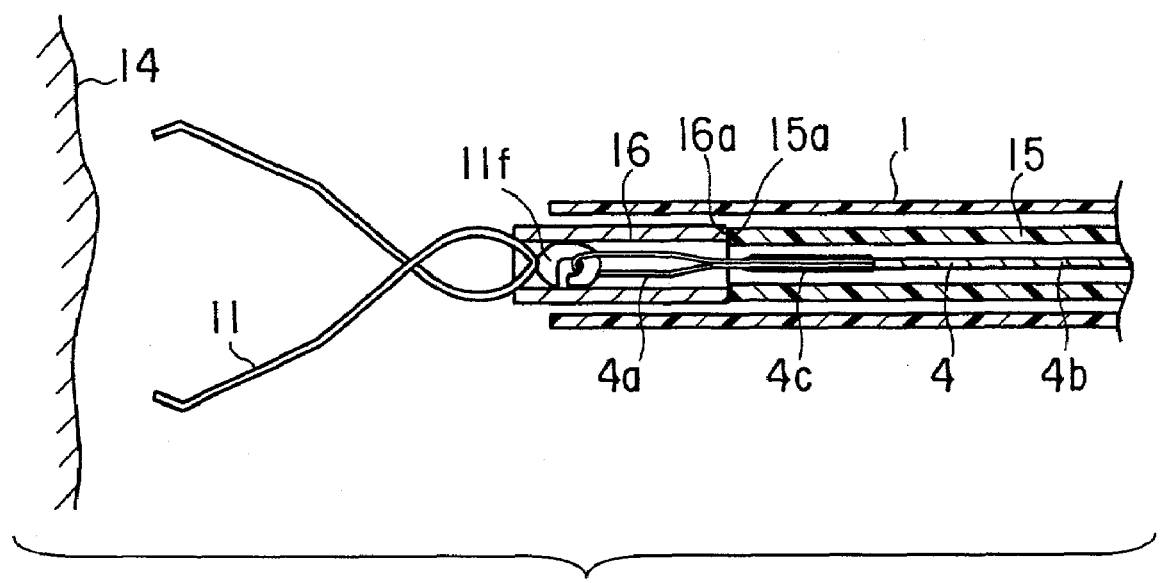
FIG. 15 is a longitudinal side view of the clip apparatus according to a seventh embodiment of the present invention.

FIG. 15 shows a seventh embodiment, the same constituting portions as those of the first embodiment are denoted with the same reference numerals, and the description thereof is omitted.

A manipulating member 15 having flexibility is inserted in the introducing tube 1 so that the member can advance or retreat. The manipulating member 15 is disposed behind a clip tightening ring 16 disposed in the introducing tube 1 as described later, and directly receives the force applied by the manipulating wire 4 during ligating with the clip 11.

The manipulating member 15 is a coil sheath which is constituted, for example, by closely winding a metal wire having a circular section (such as stainless steel) around the inner and outer surfaces having concaves/convexes. When the manipulating member 15 is moved toward the tip end with respect to the introducing tube 1, the clip 11 and the clip tightening ring 16 can be projected from the introducing tube 1.

The manipulating member 15 may be a square coil sheath which is constituted, for example, by crushing a metal wire (such as stainless steel) having a circular section, setting the wire section to be rectangular, and closely winding the wire around the smooth inner and outer surfaces. Moreover, as compared with the round coil sheath, even when the same diameter of the material wire is used, the coil sheath having a large inner diameter can be realized. Therefore, the projecting of the clip and the inserting of the manipulating wire are further facilitated.

Furthermore, the manipulating member 15 may be a tube sheath of a polymer resin (synthesized polymer polyamide, high/low density polyethylene, polyester, polytetrafluoroethylene, tetrafluoroethylene-perfluoroalkylivinylether copolymer, tetrafluoroethylene-hexafluoropropylene copolymer, and the like). Since the inner and outer surfaces of the sheath have smoothness, the inserting of the sheath in the introducing tube 1, and the inserting of the manipulating wire 4 are facilitated.

Additionally, the manipulating member 15 may be a tube sheath formed by disposing and embedding a reinforcing member in a double tube whose wall has inner and outer layers. The inner and outer layers are formed of the polymer resin. The reinforcing member is made of a cylindrical blade formed, for example, by knitting a fine metal wire in a lattice form. Therefore, as compared with the tube sheath in which the reinforcing member is not embedded, even when the force for compressing the sheath is applied to the tip end and base end of the sheath, the sheath is superior in resistance to compression and does not buckle.

The manipulating member 15 has an outer diameter which can be passed in the introducing tube 1, an inner diameter through which the manipulating wire 4 can be inserted, and an outer diameter of 3 mm or less. The inner diameter is set as large as possible. Additionally, a projecting force amount can securely be transmitted. The thickness of the member needs to be set such that the member does not buckle even under the force applied during ligating with the clip 11.

Moreover, when the clip tightening ring 16 is attached to the arm portions 11b, 11b' of the clip 11, the arm portions 11b, 11b' of the clip 11 are closed, and the ring has a substantially tubular form. The clip 11 is joined to the manipulating wire 4 by attaching the loop wire 4a to the hook 11f.

The clip tightening ring 16 is molded by injecting resins having strength (polybutylterephthalate, polyamide, polyphenyl amide, liquid crystal polymer, polyether ketone, polyphthal amide). Alternatively, the ring may be molded by injecting, cutting, or is plasticizing the metal (such as stainless steel).

Moreover, the clip tightening ring 16 has an inner diameter of 0.6 to 1.3 mm, and outer diameter of about 1.0 to 2.1 mm.

The action of the seventh embodiment will next be described. While the body cavity is observed with the endoscope, the tip end of the introducing tube 1 is guided to the living tissue 14. The clip 11 and clip tightening ring 16 disposed in the introducing tube 1 are projected from the introducing tube 1. This is realized by pushing the manipulating member 15 toward the tip end of the introducing tube 1, or by drawing the introducing tube 1 toward the base end.

When the holding portions 11c, 11c' of the clip 11 are brought close to the living tissue 14, and the manipulating wire 4 is drawn, a base end surface 16a of the clip tightening ring 16 engages with a tip end surface 15a of the manipulating member. When the manipulating wire 4 is further drawn, the elliptic portion of the base end 11a of the clip 11 is pulled into the clip tightening ring 16. Here, since the dimension of the elliptic portion is larger than the inner diameter of the clip tightening ring 16, the elliptic portion is crushed by the clip tightening ring 16. Then, the arm portions 11b, 11b' are largely extended/opened outwards.

In this state, the clip 11 is guided to hold the target living tissue 14. When the manipulating wire 4 is further drawn, the arm portions 11b, 11b' of the clip 11 are pulled into the clip tightening ring 16, and the holding portions 11c, 11c' of the clip 11 are closed. While the living tissue 14 is securely held by the arm portions 11b, 11b' of the clip, the manipulating wire 4 is further drawn, and the hook 11f is stretched, the engaging of the clip 11 and manipulating wire 4 is released. Thereby, the clip 11 which holds the living tissue 14 can be fastened in the body cavity.

According to the seventh embodiment, in addition to the effect of the sixth embodiment, the following effect is produced. A manipulating for projecting the clip from the introducing tube can more easily and securely be performed.

Figure 16:
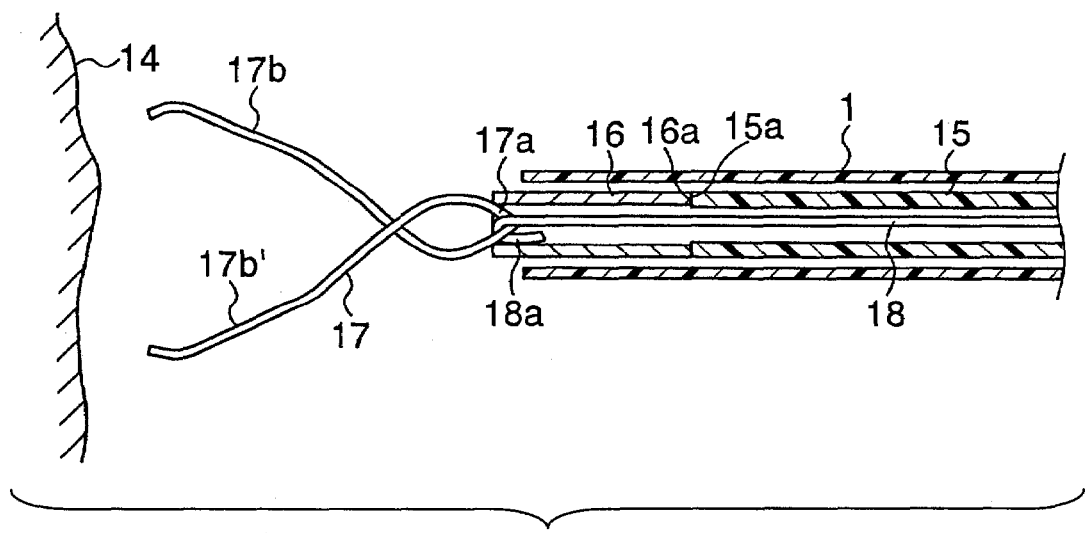
FIG. 16 is a longitudinal side view of the clip apparatus according to an eighth embodiment of the present invention.
Figure 17:
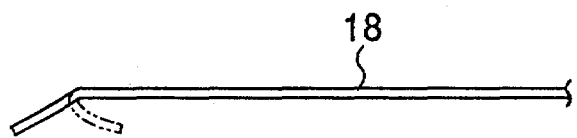
FIG. 17 is a side view of the manipulating wire according to the eighth embodiment.

FIGS. 16 and 17 show an eighth embodiment. The eighth embodiment is different from the seventh embodiment in a clip 17 and manipulating wire 18. For the clip 17, the hook 11f of the clip 11 described in the seventh embodiment is omitted. The other constitution is the same as that of the clip 11.

The manipulating wire 18 is formed of a single or twined metal wire, and has a bent tip end to form a loop portion 18a. An outer diameter is of the order of 0.1 to 0.6 mm. As shown in FIG. 16, the loop portion 18a of the manipulating wire 18 is directly joined to a base end 17a of the clip 17.

Additionally, when a force of 1 to 5 kg is applied to the loop portion 18a during ligating with the clip, as shown in FIG. 17, the loop portion 18a is substantially linearly stretched. This releases the engaging of the clip 17 and manipulating wire 18.

The action of the eighth embodiment will next be described.

When the holding portions of the clip 17 are brought close to the living tissue 14, and the manipulating wire 18 is drawn, the base end surface 16a of the clip tightening ring 16 engages with the tip end surface 15a of the manipulating member. When the manipulating wire 18 is further drawn, the elliptic portion of the base end of the clip 17 having an inner diameter larger than that of the clip tightening ring 16 is therefore crushed by the clip tightening ring 16. Then, arm portions 17b, 17b' are largely extended/opened outwards.

In this state, the clip 17 is guided to hold the target living tissue 14. When the manipulating wire 18 is further drawn, the arm portions 17b, 17b' of the clip 17 are pulled into the clip tightening ring 16, and the holding portions of the clip 17 are closed. While the living tissue 14 is securely held by the holding portions of the clip 17, the manipulating wire 18 is further drawn, and the loop portion 18a is substantially linearly stretched. This releases the engaging of the clip 17 and manipulating wire 18. Thereby, the clip 11 with the living tissue 14 held therein can be fastened in the body cavity.

According to the eighth embodiment, in addition to the effect of the seventh embodiment, the following effect is produced. Since it is unnecessary to mold the hook 11f in the base end of the clip 17, the clip 17 can be manufactured less expensively. Moreover, since the loop portion 18a of the tip end of the manipulating wire 18 is formed simply by bending the wire, the manipulating wire 18 can be molded less expensively, and can easily be joined to the base end of the clip 17.

FIGS. 18A to 18D show a ninth embodiment, and are longitudinal side views showing the action of the ligating apparatus. The same constituting portions as those of the seventh embodiment are denoted with the same reference numerals, and the description thereof is omitted. The manipulating wire 10 is passed through the manipulating member 15 such that the wire can advance or retreat.

The clip 9 has the same structure as that of the fifth embodiment shown in FIGS. 11A, 11B. The hole 21 through which the manipulating wire 10 can be inserted is formed in the base end 9a of the clip 9. The bulged portion 10a as the stopper larger than the hole 21 is disposed in the tip end of the manipulating wire 10. Furthermore, the clip tightening ring 16 formed of a cylindrical pipe is disposed between the tip end surface of the manipulating member 15 and the base end of the clip 9, while the manipulating wire 10 is inserted through the ring.

The action of the ninth embodiment will next be described.

Figure 18A:
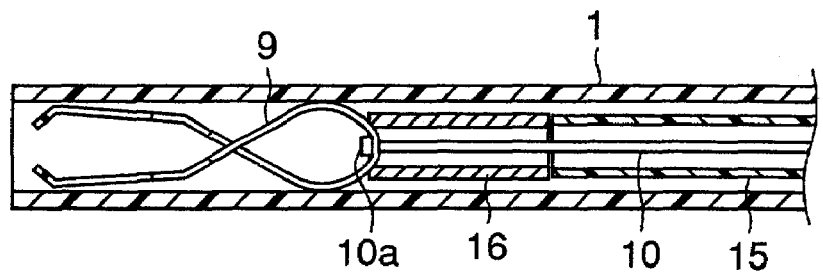
FIGS. 18A to 18D are longitudinal side views showing an action of the clip apparatus according to a ninth embodiment of the present invention.

As shown in FIG. 18A, the clip 9 is attached to the tip end of the introducing tube 1, and the manipulating member 15 abuts on the base end 9a of the clip 9 via the clip tightening ring 16 before ligating.

Figure 18B:
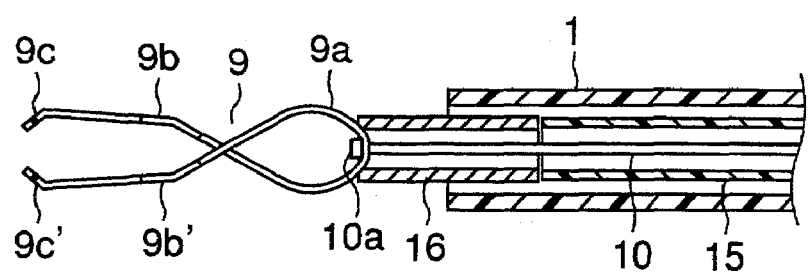
Figure 18C:
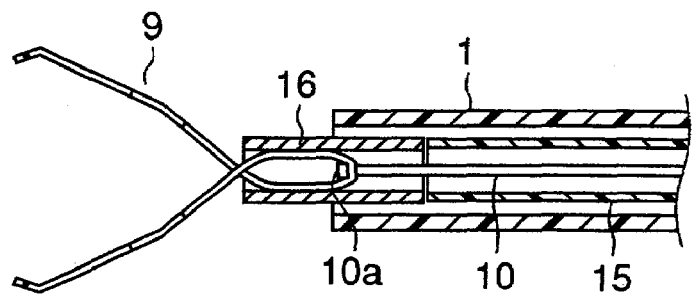

As shown in FIG. 18B, when the manipulating member 15 is advanced or the introducing tube 1 is retreated, the clip 9 and clip tightening ring 16 project from the tip end of the introducing tube 1. In this state, when the manipulating wire 10 is drawn, the base end 9a of the clip 9 is pulled into the clip tightening ring 16, and the arm portions 9b, 9b' largely extend/open as shown in FIG. 18C. In this case, the force applied by the manipulating wire 10 can securely be received by the manipulating member 15 via the clip tightening ring 16.

Figure 18D:
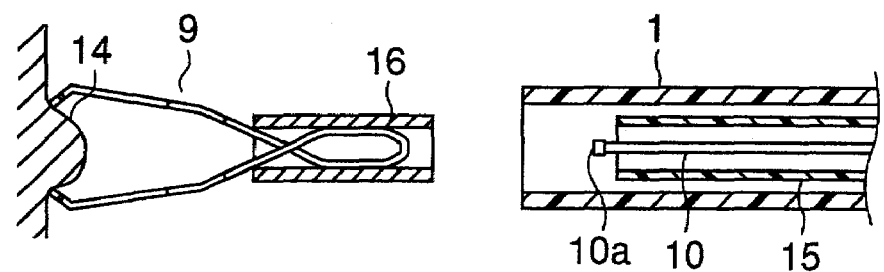

In this state, when the holding portions 9c, 9c' of the clip 9 are pressed onto the target tissue 14, and the manipulating wire 10 is further drawn, the arm portions 9b, 9b' of the clip 9 are pulled into the clip tightening ring 16, and the holding portions 9c, 9c' are closed. Thereby, as shown in FIG. 18D, the target tissue 14 can be held. When the manipulating wire 10 is further drawn, the bulged portion 10a of the tip end of the manipulating wire 10 deforms and enlarges the hole 21 of the base end 9a of the clip 9. Alternatively, the diameter of the bulged portion 10a is deformed and reduced, so that the manipulating wire 10 is separated from the clip 9. Thereby, the clip 9 can be fastened in the living tissue.

According to the ninth embodiment, the clip is directly joined to the manipulating wire, and the number of components in the engaging portion of the clip and manipulating wire decreases. Thereby, the manufacturing cost is reduced. Moreover, the attachment manipulating of the clip during manufacturing is facilitated.

Moreover, since the force applied by the manipulating wire can securely be received by the manipulating member, the living tissue can be ligated with a stronger force. Furthermore, since the clip tightening ring confines the arm portions of the clip, the living tissue can be ligated with a much stronger force.

Figure 19A:
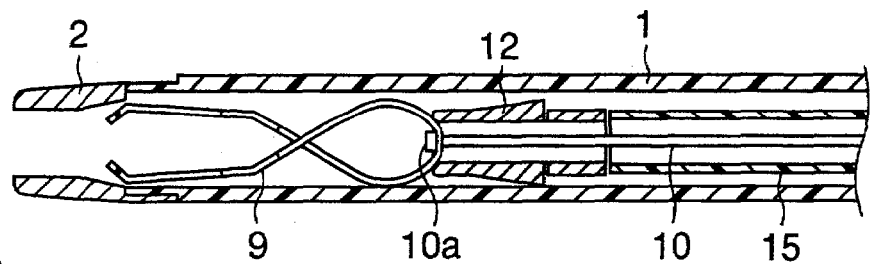
FIGS. 19A to 19C are longitudinal side views showing the action of the clip apparatus according to a tenth embodiment of the present invention.
Figure 19B:
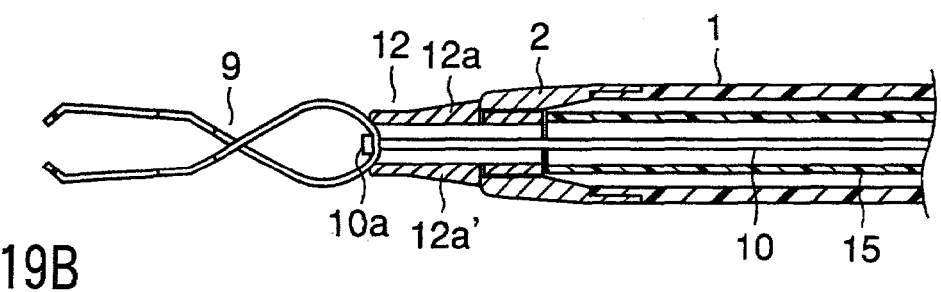
Figure 19C:
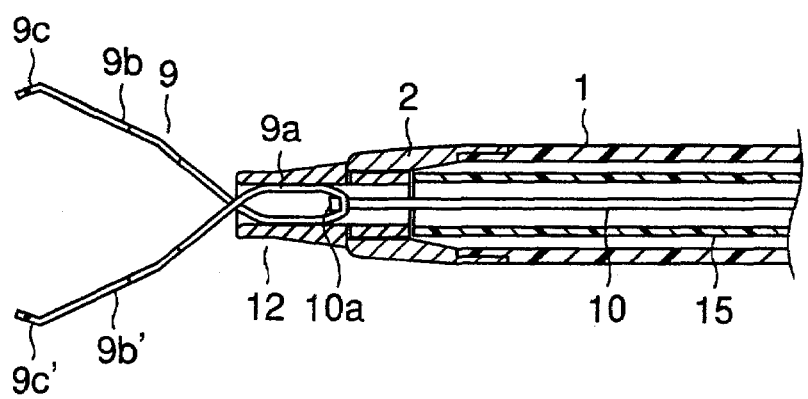

FIGS. 19A to 19C show a tenth embodiment, and are longitudinal side views showing the action of the ligating apparatus. The same constituting portions as those of the seventh embodiment are denoted with the same reference numerals, and the description thereof is omitted. The manipulating wire 10 is passed through the manipulating member 15 such that the wire can advance or retreat.

Figure 14:
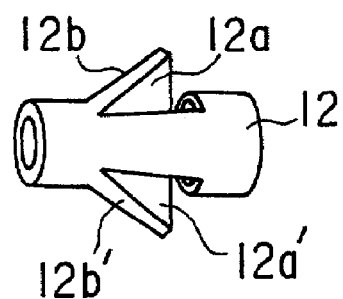
FIG. 14 is a perspective view of a clip tightening ring according to the sixth embodiment.

The clip 9 has the same structure as that of the fifth embodiment shown in FIGS. 11A, 11B and that of the ninth embodiment. The hole 21 through which the manipulating wire 10 can be inserted is formed in the base end 9a of the clip 9. The bulged portion 10a as the stopper larger than the hole 21 is disposed in the tip end of the manipulating wire 10. Furthermore, the clip tightening ring 12 as engaging means having the same structure as that of the sixth embodiment shown in FIG. 14 is disposed between the tip end surface of the manipulating member 15 and the base end of the clip 9, while the manipulating wire 10 is inserted through the ring.

The action of the tenth embodiment will next be described.

As shown in FIG. 19A, the clip 9 is attached to the tip end of the introducing tube 1, and the manipulating member 15 abuts on the base end 9a of the clip 9 via the clip tightening ring 12 before ligating.

As shown in FIG. 19B, when the manipulating member 15 is advanced or the introducing tube 1 is retreated, the clip 9 and clip tightening ring 12 project from the tip end of the introducing tube 1. In this state, when the manipulating wire 10 is drawn, the base end 9a of the clip 9 is pulled into the clip tightening ring 12, and the arm portions 9b, 9b' largely extend/open as shown in FIG. 19C. In this case, the blades 12a, 12a' of the clip tightening ring 12 are folded when passed through the tip-end chip 2. However, when the blades 12a, 12a' are passed through the tip-end chip 2, the blades project again and engage with the tip-end chip 2. Therefore, the clip tightening ring 12 can be prevented from entering the tip-end chip 2 again. The force applied by the manipulating wire 10 can securely be received by the tip-end chip 2 via the clip tightening ring 12.

In this state, similarly as the ninth embodiment, when the holding portions 9c, 9c' of the clip 9 are pressed onto the target tissue 14, and the manipulating wire 10 is further drawn, the arm portions 9b, 9b' of the clip 9 are pulled into the clip tightening ring 12, and the holding portions 9c, 9c' are closed. Thereby, the target tissue 14 can be held. When the manipulating wire 10 is further drawn, the bulged portion 10a of the tip end of the manipulating wire 10 deforms and enlarges the hole 21 of the base end 9a of the clip 9. Alternatively, the diameter of the bulged portion 10a is deformed and reduced, so that the manipulating wire 10 is separated from the clip 9. Thereby, the clip 9 can be fastened in the living tissue.

According to the tenth embodiment, in addition to the ninth embodiment, since the force applied by the manipulating wire can securely be received by the engaging means, the living tissue can be ligated with a stronger force. Moreover, since the clip tightening ring confines the arm portions of the clip, the living tissue can be ligated with a much stronger force.

FIGS. 20A to 20D show an eleventh embodiment, and are longitudinal side views showing the action of the ligating apparatus. The same constituting portions as those of the fifth embodiment are denoted with the same reference numerals, and the description thereof is omitted.

As shown in FIG. 20A, the manipulating wire is constituted by the bulged portion 11a and base end wire 10'. The base end wire 10' is welded or bonded to the manipulating wire 10. Alternatively, when the core wire of the base end wire 10' constituted of the metal twined wire is used in the manipulating wire 10, only one wire is used, the number of components decreases, and therefore the manufacturing cost can be reduced. The diameter of the base end wire 10' is of the order of 0.3 to 1.5 mm.

The clip 3 basically has the same structure as that of the first embodiment shown in FIGS. 1 to 5A, 5B, 5C. Similarly as the ninth embodiment, the hole 21 is formed in the base end 3a. A plurality of clips 3 are disposed in series in the introducing tube 1, the manipulating wire 10 is inserted through the hole 21 of each clip 3, the bulged portion a is fit in the hole 21 of a front end, and the manipulating wire 10 is prevented from dropping.

The action of the eleventh embodiment will next be described.

As shown in FIG. 20A, the plurality of clips 3 are disposed in series in the tip end of the introducing tube 1, and the bulged portion 10a is fit in the hole 21 of the front clip 3.

As shown in FIG. 20B, when the base end wire 10' is advanced or the introducing tube 1 is retreated, the front clip 3 projects from the tip end of the introducing tube 1, and the arm portions 3b, 3b' largely extend/open. In this state, when the base end wire 10' is drawn, the base end 3a of the clip 3 is pulsed into the tip-end chip 2, and the projections 3g, 3g' disposed in the arm portions 3b, 3b' of the clip 3 engage with the tip end of the tip-end chip 2 as shown in FIG. 20C. When the base end wire 10' is further drawn, the base end 3a of the clip 3 is plastically deformed, the holding portions 3c, 3c' are closed, and the target tissue 14 can be held.

When the base end wire 10' is further drawn, the bulged portion 10a of the tip end of the manipulating wire 10 deforms and enlarges the hole 21 of the base end 3a of the clip 3. Thereby, the manipulating wire 10 is separated from the clip 3, and the clip 3 can be fastened in the living tissue.

Next, when the base end wire 10' is advanced or the introducing tube 1 is retreated, the bulged portion 10a of the manipulating wire 10 engages in the hole 21 of the second clip 3, and the second clip 3 can be projected from the tip-end chip 2 on the tip end of the introducing tube 1. When a similar manipulating is repeated, the living tissue can continuously be ligated with the clip 3.

According to the eleventh embodiment, the engaging structure of the clip and manipulating wire is simplified, and the number of components can be decreased, so that the manufacturing cost can be reduced. Moreover, the attachment manipulating of the clip during manufacturing can be facilitated, and a dispersion in assembly can be prevented. Furthermore, since the clip in the introducing tube is positioned in the vicinity of a center by the manipulating wire, the clip projects by a small force amount. Moreover, the ligating of the tissue with the clip can be continuously performed simply by drawing one base end wire, and operability can therefore be enhanced.

Moreover, when the holding portions 3c, 3c' of the clip 3 hold the tissue, the target tissue 14 cannot securely be held in some case. Alternatively, the tissue different from the targeted tissue is grasped by the clip 3 in some case. In this case, the clip 3 having the holding portions 3c, 3c' once closed is extended/opened again, the tissue is targeted again, and the clip 3 is sometimes closed again.

The base end wire 10' is slightly drawn from the state shown in FIG. 20B. While the tissue is held between the holding portions 3c, 3c' of the clip 3, and the clip 3 needs to be extended/opened again, the opening of the clip is realized by the following action. That is, the base end wire 10' is pushed forwards, or pulled toward the base end of the introducing tube 1, so that the arm portions 3b, 3b' of the clip 3 are extended/opened. In this case, the base end 3a of the clip 3 is not plastically deformed yet. Therefore, the arm portions 3b, 3b' of the clip 3 can be extended/opened by the elastic force given beforehand. In this case, the target tissue 14 can be targeted and grasped by the clip 3 again.

The treatment tool for the endoscope usually has a total length of 1000 mm or more and is very long. Therefore, it is difficult to package the tool in a straightened state, and the introducing tube 1 is packaged in a small rolled state. To set a package case to be smaller, it is general to roll and package the introducing tube 1 to be as small as possible. However, in the ligating apparatus in which the plurality of clips 3 are disposed as described above, when the introducing tube 1 is largely bent during packaging, the clip 3 disposed in the introducing tube 1 is possibly deformed and broken, and possibly the clip cannot sufficiently fulfill the function.

On the other hand, as shown in FIG. 20D, a minimum bend radius r of a curved portion 32 of the tip end of an endoscope 31 is about 15 mm. Therefore, the clip 3 has to be designed not to be deformed or broken, even when the introducing tube 1 of the ligating apparatus is bent to the bend radius r of 15 mm at minimum. Thereby, in the ligating apparatus in which the plurality of clips 3 are disposed, the introducing tube 1 with the clips 3 disposed therein needs to be packaged at the bend radius r of 15 mm or more, or in the straightened state.

Moreover, when the introducing tube 1 of the ligating apparatus is inserted in the forceps channel of the endoscope 31, and the introducing tube 1 including the clips 3 is disposed behind the curved portion 32 of the endoscope 31, it is very difficult to project the clips 3 from the introducing tube 1. The curved portion 32 of the endoscope 31 forms a large resistance, and the clip 3 disposed in the base end of the introducing tube 1 cannot be moved in a tip end direction of the introducing tube 1. Thereby, the introducing tube 1 including the clip 3 has to be disposed before the curved portion 32 of the endoscope 31. In general, the length of the curved portion 32 of the endoscope 31 is about 120 mm from the tip end of the endoscope.

On the other hand, the introducing tube 1 inserted in the forceps channel of the endoscope 31 needs to be projected to a position in a view field of the endoscope 31 from the tip end of the endoscope. (The length to the tip end of the introducing tube from the tip end of the endoscope is called a minimum visible distance L.) In general, the minimum visible distance L of the endoscope 31 is about 5 mm. Therefore, the introducing tube 1 including the clips 3 is not disposed in the curved portion 32 of the endoscope 31 in a position projecting from the tip end of the endoscope by at least 5 mm. Thereby, all the clips 3 need to be disposed in a position of 125 mm or less from the tip end of the introducing tube 1 of the ligating apparatus.

FIGS. 21A to 21D show a twelfth embodiment, and are longitudinal side views showing the action of the ligating apparatus. The same constituting portions as those of the ninth embodiment are denoted with the same reference numerals, and the description thereof is omitted.

A plurality of clips 9 and a plurality of clip tightening rings 16 are alternately disposed in series in the introducing tube 1. The clip 9 and clip tightening ring 16 have the same structure as that of the ninth embodiment shown in FIGS. 18A to 18D, and the hole 21 through which the manipulating wire 10 can be inserted is formed in the base end 9a of the clip 9. The bulged portion 10a as the stopper larger than the hole 21 is disposed in the tip end of the manipulating wire 10.

Furthermore, the clip tightening ring 16 formed of the cylindrical pipe through which the manipulating wire 10 is inserted is disposed between the tip end surface of the manipulating member 15 and the base end of the clip 9. The manipulating wire 10 is inserted through the hole 21 of the clip 9, the bulged portion 10a is fit in the hole 21 of the front clip 9, and the manipulating wire 10 is stopped from dropping.

The action of the twelfth embodiment will next be described.

Figure 21A:
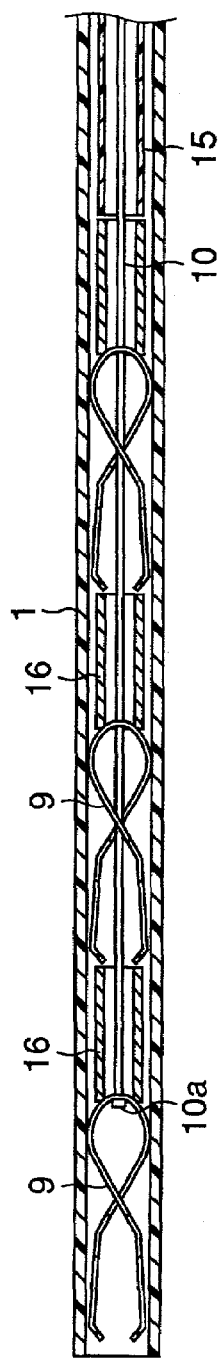
FIGS. 21A to 21D are longitudinal side views showing the action of the clip apparatus according to a twelfth embodiment of the present invention.

As shown in FIG. 21A, the plurality of clips 9 and the plurality of clip tightening rings 16 are alternately disposed in series in the introducing tube 1, and the tip end of the manipulating member 15 abuts on the base end of the rearmost clip tightening ring 16 before ligating.

Figure 21B:
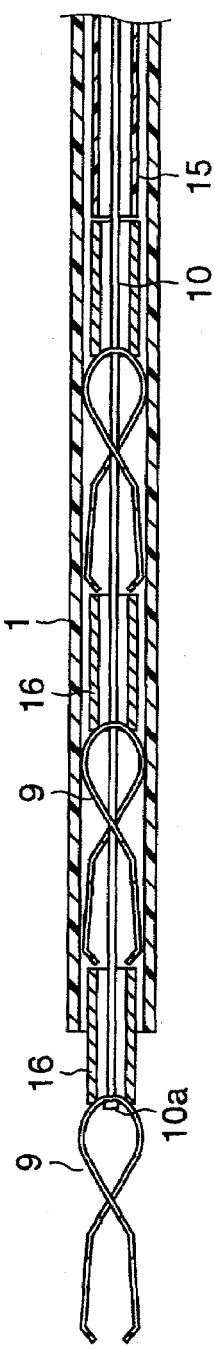
Figure 21C:
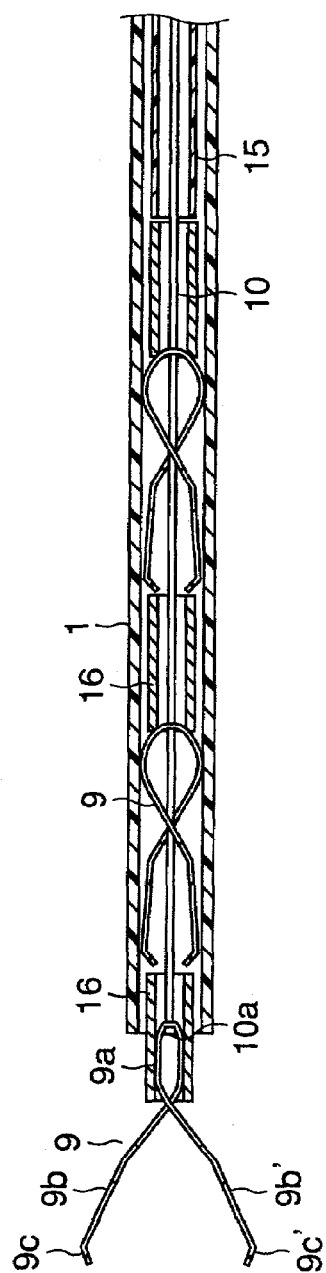

As shown in FIG. 21B, when the manipulating member 15 is advanced or the introducing tube 1 is retreated, the front clip 9 and clip tightening ring 16 project from the tip end of the introducing tube 1. In this state, when the manipulating wire 10 is drawn, the base end 9a of the clip 9 is pulled into the clip tightening ring 16, and the arm portions 9b, 9b' of the clip largely extend/open as shown in FIG. 21C. In this case, the force applied by the manipulating wire 10 can securely be received by the manipulating member 15 via the clip tightening ring 16.

Figure 21D:
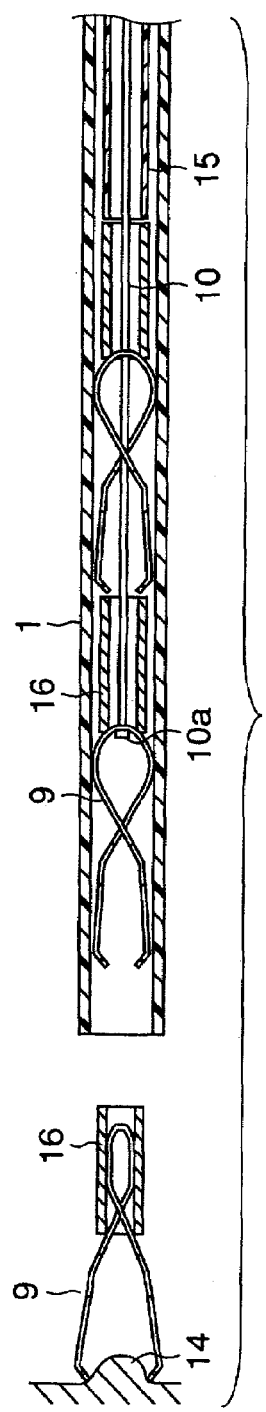

In this state, when the holding portions 9c, 9c' of the clip 9 are pressed onto the target tissue 14, and the manipulating wire 10 is further drawn, the arm portions 9b, 9b' of the clip 9 are pulled into the clip tightening ring 16, and the holding portions 9c, 9c' are closed. Thereby, as shown in FIG. 21D, the target tissue 14 can be held. When the manipulating wire 10 is further drawn, the bulged portion 10a of the tip end of the manipulating wire 10 deforms and enlarges the hole 21 of the base end 9a of the clip 9, and manipulating wire 10 is separated from the clip 9. Thereby, the clip 9 can be fastened in the living tissue.

Subsequently, when the manipulating member 15 is advanced or the introducing tube 1 is retreated, the bulged portion 10a of the manipulating wire 10 is engaged in the hole 21 of the second clip 9, and the second clip 9 can be projected from the tip end of the introducing tube 1. When the similar manipulating is repeated, the living tissue can continuously be ligated with the clip 9.

According to the twelfth embodiment, in addition to the effect of the eleventh embodiment, the force applied by the manipulating wire can be securely received by the manipulating member, and the living tissue can be ligated with a stronger force. Moreover, since the clip tightening ring confines the arm portions of the clip 3, the living tissue can be ligated with a much stronger force.

Figure 22A:
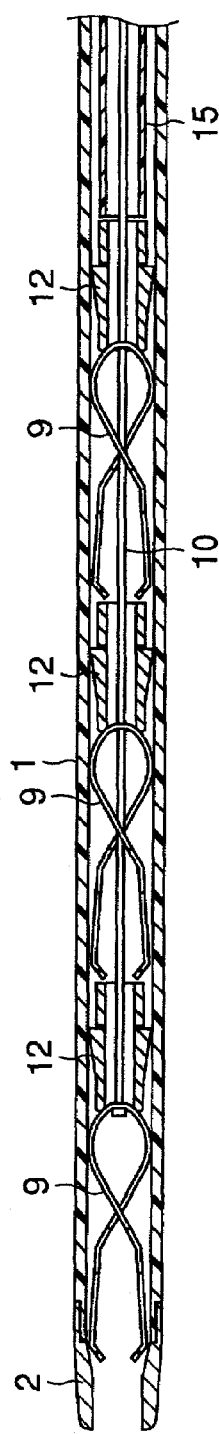
FIGS. 22A to 22C are longitudinal side views showing the action of the clip apparatus according to a thirteenth embodiment of the present invention.
Figure 22B:
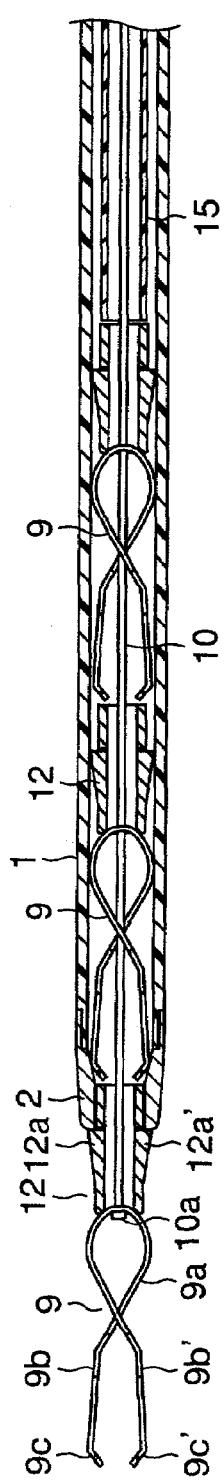
Figure 22C:
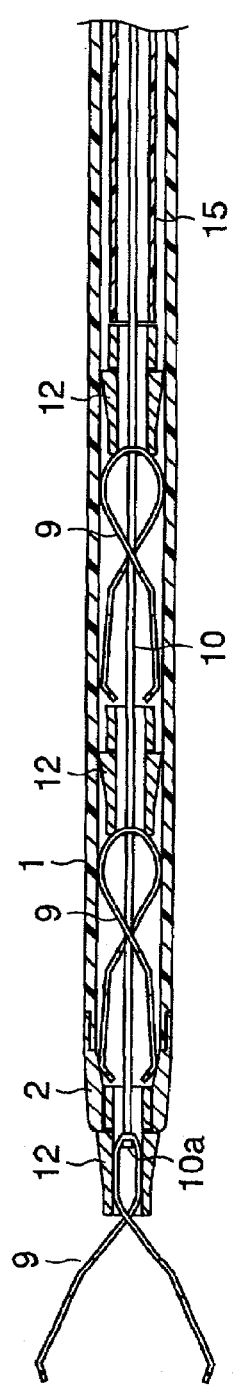

FIGS. 22A to 22C show a thirteenth embodiment, and are longitudinal side views showing the action of the ligating apparatus. The same constituting portions as those of the tenth embodiment are denoted with the same reference numerals, and the description thereof is omitted.

The plurality of clips 9 and the plurality of clip tightening rings 12 are alternately disposed in series in the introducing tube 1. The clip 9 and clip tightening ring 12 have the same structure as that of the tenth embodiment shown in FIGS. 19A to 19C, and the hole 21 through which the manipulating wire 10 can be inserted is formed in the base end 9a of the clip 9. The bulged portion 10a as the stopper larger than the hole 21 is disposed in the tip end of the manipulating wire 10. Furthermore, the clip tightening ring 12 as engaging means having the same structure as that of the tenth embodiment is disposed between the tip end surface of the manipulating member 15 and the base end of the clip 9, while the manipulating wire 10 is inserted through the ring.

The action of the thirteenth embodiment will next be described.

Figure 23A:
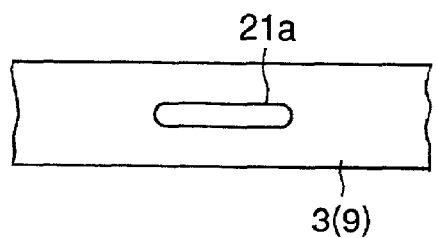
FIGS. 23A to 23D are front views of modification examples of a hole formed in a base end of the clip according to a fourteenth embodiment of the present invention.

As shown in FIG. 23A, the plurality of clips 9 and the plurality of clip tightening rings 12 are alternately disposed in series in the introducing tube 1, and the tip end of the manipulating member 15 abuts on the base end 9a of the rearmost clip tightening ring 12 before ligating.

Figure 23C:
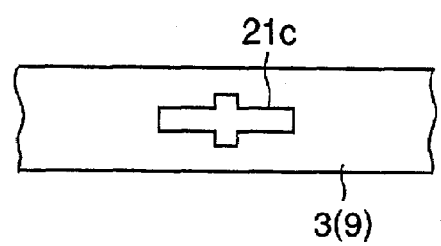
Figure 23B:
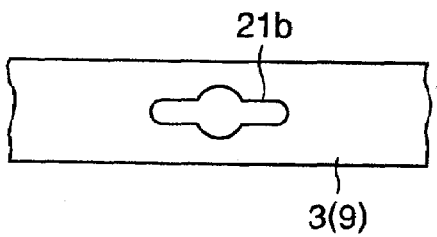

As shown in FIG. 23B, when the manipulating member 15 is advanced or the introducing tube 1 is retreated, the front clip 9 and clip tightening ring 12 project from the tip end of the introducing tube 1. In this state, when the manipulating wire 10 is drawn, the base end 9a of the clip 9 is pulled into the clip tightening ring 12, and the arm portions 9b, 9b' of the clip 9 largely extend/open as shown in FIG. 23C. In this case, the blades 12a, 12a' of the clip tightening ring 12 are folded when passed through the tip-end chip 2. However, when the blades 12a, 12a' are passed through the tip-end chip 2, the blades project again and engage with the tip-end chip 2. Therefore, the clip tightening ring 12 can be prevented from entering the tip-end chip 2 again. The force applied by the manipulating wire 10 can securely be received by the tip-end chip 2 via the clip tightening ring 12.

In this state, similarly as the ninth embodiment, when the holding portions 9c, 9c' of the clip 9 are pressed onto the target tissue 14, and the manipulating wire 10 is further drawn, the arm portions 9b, 9b' of the clip 9 are pulled into the clip tightening ring 12, and the holding portions 9c, 9c' are closed. Thereby, the target tissue 14 can be held. When the manipulating wire 10 is further drawn, the bulged portion 10a of the tip end of the manipulating wire 10 deforms and enlarges the hole 21 of the base end 9a of the clip 9, and the manipulating wire 10 is separated from the clip 9. Thereby, the clip 9 can be fastened in the living tissue. Subsequently, when the manipulating member 15 is advanced or the introducing tube 1 is retreated, the bulged portion 10a of the manipulating wire 10 engages in the hole 21 of the second clip 9, and the second clip 9 can be projected from the tip end of the introducing tube 1. When the similar manipulating is repeated, the living tissue can continuously be ligated with the clip 9.

According to the thirteenth embodiment, in addition to the effect of the eleventh embodiment, since the force applied by the manipulating wire can securely be received by the engaging means, the living tissue can be ligated with a stronger force. Moreover, since the clip tightening ring confines the arm portions of the clip, the living tissue can be ligated with a much stronger force.

Figure 23D:
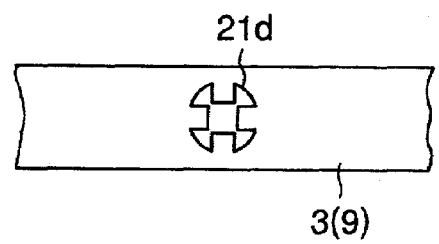

FIGS. 23A to 23D show a fourteenth embodiment, and modification examples of the hole 21 formed in the base end 3a, 9a of the clip 3, 9. FIG. 23A shows an elongated slit. The elongated slit has a length of about 0.5 to 1.5 mm, and a height of about 0.2 to 0.7 mm. FIG. 23B shows a round hole formed in the middle portion of the elongated slit. The elongated slit has a length of about 0.5 to 1.5 mm, and a height of about 0.2 to 0.6 mm, and the diameter of the round hole is of the order of 0.3 to 0.7 mm and is larger than the height of the elongated slit. FIG. 23C shows a cross-shaped slit. The cross-shaped slit has a length of about 0.5 to 1.5 mm, a height of about 0.3 to 0.7 mm, and a width of about 0.15 to 0.4 mm. FIG. 23D shows four pieces projecting toward the middle portion from the inner peripheral portion of the round hole. The round hole has a diameter of about 0.4 to 0.7 mm, and the projecting piece has a height of about 0.15 to 0.3 mm. When only the round hole is formed, the bulged portion abuts on the whole periphery of the round hole. A large force amount for deforming the hole is sometimes required, and a doctor and assistant require a strong force for ligating the tissue with the clip. With the hole shapes of the FIGS. 23A to 23D, the portion easily deformed when abutting on the bulged portion is formed, and deformed with a moderate force amount. Therefore, the doctor and assistant can ligate the tissue with the clip with an adequate force.

FIGS. 24A to 28B show a fifteenth embodiment, and modification examples of the bulged portion disposed in the tip end of the manipulating wire 10. FIGS. 24A, 24B show a flat bulged portion 10b formed by crushing the tip end of the manipulating wire 10 to be flat. The flat bulged portion 10b is necessarily larger than the hole of the clip base end, and has a width of about 0.4 to 1 mm, thickness of about 0.2 to 0.7 mm, and length of about 0.3 to 3 mm. FIGS. 25A, 25B show that a pipe-shaped member 10c is attached to the tip end of the manipulating wire 10 to form the bulged portion. The pipe-shaped member 10c is welded or bonded. The diameter of the bulged portion is necessarily larger than that of the hole of the clip base end, and is of the order of 0.25 to 1 mm. The bulged portion has a length of about 0.25 to 3 mm. FIGS. 26A, 26B show a bulged portion 10d formed by caulking and processing the tip end of the manipulating wire 10 in a conical shape. The diameter of the bulged portion 10d is necessarily larger than that of the hole of the clip base end, and is of the order of 0.25 to 1 mm. The bulged portion 10d has a length of about 0.25 to 3 mm. FIGS. 27A, 27B show a bulged portion 10e formed by heating and processing the tip end of the manipulating wire 10 in a spherical shape. The diameter of the bulged portion 10e is necessarily larger than that of the hole of the clip base end, and is of the order of about 0.25 to 1 mm. FIGS. 28A, 28B show a bulged portion 10f formed by bending back the tip end of the manipulating wire 10. The diameter of the manipulating wire is of the order of 0.15 to 1 mm and is necessarily larger than that of the hole of the clip base end when bent. Moreover, the bent-back length of the bulged portion 10f is of the order of 0.5 to 3 mm. According to the fifteenth embodiment, the bulged portion can easily be formed and the cost can be reduced. Moreover, in FIGS. 25A, 25B, the dimension of the bulged portion can easily be controlled, and the ligating force amount can be stabilized.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A ligating apparatus comprising:
   an introducing tube which is inserted in a living body cavity;
   a manipulating wire inserted through the introducing tube in such a manner that the manipulating wire is movable in advancing and retreating directions;
   a clip having a base end and at least two arm portions extending from the base end, each of the arm portions having a holding portion apart from the base end, and the base end having a through hole which is extended in the advancing direction and through which said manipulating wire is inserted, the manipulating wire including a tip end which is projected from the through hole and positioned between the arm portions; and
   a stopper having a bulged portion formed at the tip end of the manipulating wire, the bulged portion having a larger diameter or width than that of the through hole so that the bulged portion engages with the base end;
   wherein the base end and/or bulged portion is deformed when the manipulating wire is moved in the retreating direction against the base end of the clip, so that the diameter or width of the bulged portion becomes relatively smaller than that of the through hole and is disengaged with the base end whereby the tip end of the manipulating wire is removed from the base end through the through hole.

2. A ligating apparatus according to claim 1, further comprising a clip tightening ring attached to the arm portions of said clip to close the holding portions of the clip; and a manipulating member for the clip tightening ring, inserted through the introducing tube disposed behind the clip tightening ring in such a manner that the manipulating member can freely advance or retreat.

3. A ligating apparatus according to claim 1, further comprising a clip tightening ring attached to the arm portions of said clip to close the holding portions of the clip; the clip and clip tightening ring being inserted in the introducing tube so as to be projected from the tip portion of the introducing tube;
   abutting members respectively disposed on an end portion of the introducing tube and the clip tightening ring, for prohibiting the clip tightening ring projected from the tip portion of the introducing tube, from being into the introducing tube, when the clip and the clip tightening ring are moved in the retracting direction project forwards from the introducing tube; and
   a manipulating member inserted through the introducing tube disposed behind the clip tightening ring in such a maimer that the manipulating member can freely advance to move the clip tightening ring.

4. A ligating apparatus according to claim 1, wherein the tip end of said manipulating wire is crushed in a flat shape, to form the bulged portion.

5. A ligating apparatus according to claim 1, wherein a pipe-shaped member is attached to the tip end of said manipulating wire to form the bulged portion.

6. A ligating apparatus according to claim 1, wherein the through hole is linearly extended through the base end, and a portion of the manipulating wire which is inserted through the through hole is linear and extended in the advancing direction.

7. A ligating apparatus according to claim 1, wherein the base of the clip is formed by a strip having a thickness, and an extending direction of the through hole corresponds to a thickness direction of the base.

8. A ligating apparatus comprising:
   an introducing tube which can be inserted in a living body cavity;
   a manipulating wire inserted through the introducing tube in such a manner that the manipulating wire can freely advance or retreat; and
   at least two clips each of which has a base end, a plurality of arm portions extending from the base end and holding portions formed on the arm portions apart from the base end, wherein two or more clips are arranged in series, holes through which said manipulating wire can be inserted are formed through the base ends of respective clips, and a stopper portion larger than the hole is disposed in a tip end of the manipulating wire inserted through the holes in the base ends of the at least two clips.

9. A ligating apparatus according to claim 8, wherein a clip tightening ring attached to the arm portions of said clip to close the holding portions of the clip; and a manipulating member inserted through the introducing tube disposed behind the clip tightening ring disposed in a closest position in such a manner that the manipulating member can freely advance or retreat.

10. A ligating apparatus according to claim 8, wherein a clip tightening ring attached to the arm portions of said clip to close the holding portions of the clip; the clip and clip tightening ring being inserted in the introducing tubes so as to be projected form the tip portion of the introducing tube;
    abutting members respectively, disposed on an end portion of the introducing tube and the clip tightening ring, for prohibiting the clip tightening ring projected from the tip portion of the introducing tube, from being into the introducing tube, when the clip and the clip tightening ring are moved in the retracting direction project forwards from the introducing tube; and a manipulating member inserted through the introducing tube disposed behind the clip tightening ring disposed in the closest position in such a manner that the manipulating member can freely advance or retreat.

11. A ligating apparatus according to claim 8, wherein the tip end of said manipulating wire is crushed in a flat shape, to form the stopper portion including a bulged portion.

12. A ligating apparatus according to claim 8, wherein a pipe-shaped member is attached to the tip end of said manipulating wire, and a bulged portion is formed.

13. A ligating apparatus according to claim 8, wherein the through hole of the base end has a diameter smaller than that of the stopper portion.

14. A ligating apparatus according to claim 13, wherein the through hole of the base end is deformed to increase the diameter thereof, when the manipulating wire is moved in the retreating direction against the base end of the clip.

15. A ligating apparatus according to claim 13, wherein the engaging portion of the manipulating wire is deformed to decrease the diameter thereof, when the manipulating wire is moved in the retreating direction against the base end of the clip.

16. A ligating apparatus comprising:
   a manipulating wire inserted through a longitudinal introducing tube in such a manner that the manipulating wire is movable along a longitudinal axis of the manipulating tube in advancing and retreating directions, the manipulating wire having a tip end, and a linear potion extended along the longitudinal axis and connected to the tip portion at its one end; and
   a clip having a base end and arm portions extending from the base end, each of the arm portions having a holding portion apart from the base end, the base end having inner and outer surface portions apart from each other in the longitudinal axis, and a through hole extended to the inner surface portion from the outer surface portion,
   wherein the linear portion of the manipulating wire is inserted in the through hole of the base portion so that the tip end of the manipulating wire is projected from the inner surface portion of the base end, positioned between the arm portions, and engaged with the inner surface portion of the base end, and
   wherein the base end and/or tip end is deformed when the manipulating wire is moved in the retreating direction, so that the tip end of the manipulating wire is disengaged with the inner surface portion of the base end of the clip whereby the tip end of the manipulating wire is removed from the base end through the through hole.

17. A ligating apparatus according to claim 16, wherein the tip end of the manipulating wire includes a laterally extended portion having a width larger than a diameter of the through hole.

* * * * *